US009000212B2

(12) United States Patent
Touge et al.

(10) Patent No.: US 9,000,212 B2
(45) Date of Patent: Apr. 7, 2015

(54) METHOD FOR PRODUCING COMPOUND WITH CARBONYL GROUP BY USING RUTHENIUM CARBONYL COMPLEX HAVING TRIDENTATE LIGAND AS DEHYDROGENATION OXIDATION CATALYST

(75) Inventors: Taichiro Touge, Hiratsuka (JP); Kunimori Aoki, Chigasaki (JP); Hideki Nara, Fujisawa (JP); Wataru Kuriyama, Tokyo (JP)

(73) Assignee: Takasago International Corporation, Tokyo (JP)

( * ) Notice: Subject to any disclaimer, the term of this patent is extended or adjusted under 35 U.S.C. 154(b) by 0 days.

(21) Appl. No.: 14/113,326

(22) PCT Filed: Apr. 18, 2012

(86) PCT No.: PCT/JP2012/061005
§ 371 (c)(1),
(2), (4) Date: Jun. 30, 2014

(87) PCT Pub. No.: WO2012/144650
PCT Pub. Date: Oct. 26, 2012

(65) Prior Publication Data
US 2014/0303374 A1 Oct. 9, 2014

(30) Foreign Application Priority Data

Apr. 22, 2011 (JP) ................................ 2011-095728

(51) Int. Cl.
*C07D 453/02* (2006.01)
*C07C 51/265* (2006.01)
*C07C 51/29* (2006.01)
*B01J 31/22* (2006.01)
*C07C 67/40* (2006.01)
*C07B 33/00* (2006.01)
*C07F 15/00* (2006.01)
*C07C 45/29* (2006.01)
*C07F 17/02* (2006.01)
*C07C 51/235* (2006.01)
*C07C 51/255* (2006.01)

(52) U.S. Cl.
CPC ............ *B01J 31/2295* (2013.01); *C07C 67/40* (2013.01); *C07D 453/02* (2013.01); *C07B 33/00* (2013.01); *C07F 15/0046* (2013.01); *C07C 45/29* (2013.01); *C07F 17/02* (2013.01); *C07C 51/235* (2013.01); *C07C 51/255* (2013.01); *C07C 51/265* (2013.01); *C07C 51/29* (2013.01)

(58) Field of Classification Search
CPC ..... C07F 17/02; C07F 15/0046; C07C 45/29; C07C 51/235; C07C 51/255; C07C 67/40; C07C 69/24; C07B 33/00

USPC ........... 560/239; 562/410, 420, 540; 568/309, 568/323, 375, 376, 420
See application file for complete search history.

(56) References Cited

U.S. PATENT DOCUMENTS

2005/0107638 A1  5/2005  Abdur-Rashid
2011/0237814 A1  9/2011  Kuriyama et al.

FOREIGN PATENT DOCUMENTS

| CN | 102177170 A | 9/2011 |
| CN | 103237779 A | 8/2013 |
| EP | 2492275 A1 | 8/2012 |
| JP | 2012-67021 | 4/2012 |
| WO | 2011048727 A1 | 4/2011 |
| WO | 2012039098 A1 | 3/2012 |

OTHER PUBLICATIONS

International Preliminary Report on Patentability issued on Oct. 31, 2013 in PCT/JP2012/061005.
Nielsen et al., "Efficient Hydrogen Production from Alcohols under Mild Reaction Conditions", Angew. Chem. Int. Ed., vol. 50, No. 42, pp. 9593-9597 (2011).
Zhang et al., "Synthesis and Coordination Chemistry of the New Unsymmetrical Ligand Ph2PCH2NHC2H4PPh2", Eur. J. Inorg. Chem., pp. 1635-1646 (2002).
Clelnligil-Cetin et al., "Decarbonylation of Acetone and Carbonate at a Pincer-Ligated Ru Center", Organometallics, vol. 24, No. 2, pp. 186-189 (2005).
Muthaiah et al., "Direct Amide Synthesis from Either Alcohols or Aldehydes with Amines: Activity of Ru(II) Hydride and Ru(0) Complexes", J. Org. Chem., vol. 75, pp. 3002-3006 (2010).
Zhang et al., "Well-Defined N-Heterocyclic Carbene Based Ruthenium Catalysts for Direct Amide Synthesis from Alcohols and Amines", Organometallics, vol. 29, pp. 1374-1378 (2010).

(Continued)

*Primary Examiner* — Sikarl Witherspoon
(74) *Attorney, Agent, or Firm* — Mintz Levin Cohn Ferris Glovsky and Popeo, P.C.; Peter F. Corless; Christopher R. Cowles

(57) ABSTRACT

Provided by the present invention is a method for efficient oxidation of alcohols by using, as a catalyst for dehydrogenation oxidation, a ruthenium complex which can be easily produced and easily handled and is obtainable at a relatively low cost. The invention relates to a method of producing a compound having a carbonyl group by dehydrogenation oxidation of alcohols by using as a catalyst the ruthenium carbonyl complex represented by the following general formula (1) RuXY(CO)(L) (1) (in the general formula (1), X and Y may be the same or different from each other and represent an anionic ligand, and L represents a tridentate aminodiphosphine ligand).

7 Claims, No Drawings

(56) References Cited

OTHER PUBLICATIONS

Gunanathan et al., "Direct Conversion of Alcohols to Acetals and H2 Catalyzed by an Acridine-Based Ruthenium Pincer Complex", J. Am. Chem. Soc., vol. 131, pp. 3146-3147 (2009).

Ghosh et al., "Direct Amide Synthesis from Alcohols and Amines by Phosphine-Free Ruthenium Catalyst Systems", Adv. Synth. Catal., vol. 351, pp. 2643-2649 (2009).

Baratta et al., "Pincer and Diamine Ru and Os Diphosphane Complexes as Efficient Catalysts for the Dehydogenation of Alcohols to Ketones", Chem. Eur. J., vol. 17, pp. 3474-3481 (2011).

Nova et al., "An Experimental-Theoretical Study of the Factors That Affect the Switch Between Ruthenium—Catalyzed Dehydrogenative Amide Formation versus Amine Alkylation", Organometallics, vol. 29, pp. 6548-6558 (2010).

Dam et al., "Amide Synthesis from Alcohols and Amines Catalyzed by Ruthenium N-Heterocyclic Carbene Complexes", Chem. Eur. J., vol. 16, pp. 6820-6827 (2010).

Nordstrom et al., "Amide Synthesis from Alcohols and Amines by the Extrusion of Dihydrogen", J. Am. Chem. Soc., vol. 130, pp. 17672-17673 (2008).

Gunanathan et al., "Direct Synthesis of Amides from Alcohols and Amines with Liberation of H2", Science, vol. 317, pp. 790-792 (2007).

Wise et al., "Oxidation of alcohols by transfer hydrogenation: driving the equilibrium with an intramolecular trap", Tetrahedron Letters, vol. 48, pp. 3639-3641 (2007).

Yi et al., "Highly Cooperative Tetrametallic Ruthenium-m-Oxo-m-Hydroxo Catalyst for the Alcohol Oxidation Reaction", Organometallics, vol. 25, pp. 1047-1051 (2006).

Zhao et al., "Acceptorless, Neat, Ruthenium—Catalyzed Dehydrogenative Cyclization of Diols to Lactones", Organometallics, vol. 24, pp. 2441-2446 (2005).

Zhang et al., "Facile Conversion of Alcohols into Esters and Dihydrogen Catalyzed by New Ruthenium Complexes", J. Am. Chem. Soc., vol. 127, pp. 10840-10841 (2005).

Gaithier et al., "A Heterobimetallic Rhodium (I)-Ruthenium (II) Catalyst for the Oppenauer-Type Oxidation of Primary and Secondary Alcohols under Mild Conditions", Organometallics, vol. 23, pp. 3769-3771 (2004).

Nishibayashi et al., "Oxidative Kinetic Resolution of Racemic Alcohols Catalyzed by Chiral Ferrocenyloxazolinylphosphine-Ruthenium Complexes", J. Org. Chem., vol. 68, pp. 5875-5880 (2003).

Hashiguchi et al., "Kinetic Resolution of Racemic Secondary Alcohols by Ru11-Catalyzed Hydrogen Transfer", Angew. Chem. Int. Ed., vol. 36, No. 3, pp. 288-290 (1997).

Almeida et al., "Ruthenium(ll)-Catalyzed Oppenauer-Type Oxidation of Secondary Alcohols", Chem. Eur. J., vol. 2, No. 12, pp. 1533-1536 (1996).

Wang et al., "Ruthenium-catalyzed Oxidation of Alcohols by Acetone", J. Chem. Soc., pp. 337-339 (1992).

Murahashi et al., "Ruthenium-Catalyzed Oxidative Transformation of Alcohols and Aldehydes to Esters and Lactones", J. Org. Chem., vol. 52, pp. 4319-4327 (1987).

Ito et al., "An Efficient Oxidative Lactonization of 1,4-Diols Catalyzed by CpRu(PN) Complexes", Organic Letters, vol. 9, No. 9, pp. 1821-1824 (2007).

Chinese Office Action issued on Jul. 23, 2014 in corresponding Chinese Application Ser. No. 201280019779.0 (8 pages).

English translation of Chinese Office Action issued on Jul. 23, 2014 in corresponding Chinese Application Ser. No. 201280019779.0 (8 pages).

Marcello Bertoli et al., "Osmium and Ruthenium Catalysts for Dehydrogenation of Alcohols", Organometallics, vol. 30, No. 13, Jul. 11, 2011, pp. 3479-3482.

Denis Spasyuk et al., "From Esters to Alcohols and Back with Ruthenium and Osmium Catalysts", Angewandte Chemie International Edition, vol. 51, No. 11, Mar. 12, 2012, pp. 2772-2775.

Supplementary European Search Report for corresponding Application No. EP 12773642, dated Jul. 25, 2014, 7 pages.

METHOD FOR PRODUCING COMPOUND WITH CARBONYL GROUP BY USING RUTHENIUM CARBONYL COMPLEX HAVING TRIDENTATE LIGAND AS DEHYDROGENATION OXIDATION CATALYST

CROSS-REFERENCES TO RELATED APPLICATIONS

This application is a 35 U.S.C. §371 U.S. national entry of International Application PCT/22012/061005 (WO 2012/144650) having an International filing date of Apr. 18, 2012, which claims under 35 U.S.C. §119(a) the benefit of Japanese Application No. 2011-095728, filed Apr. 22, 2011, the entire contents of which are incorporated herein by reference.

TECHNICAL FIELD

The present invention relates to a method for producing a compound with a carbonyl group by using, as a dehydrogenation oxidation catalyst, a ruthenium carbonyl complex having a tridentate ligand containing two phosphino groups and a —NH— group.

BACKGROUND ART

Compounds having a carbonyl group are important in industrial fields. Examples of known methods for producing a carbonyl compound by using an oxidation reaction include a method of oxidizing alcohols with chromic acid, a method of oxidizing by using tetrapropylammonium perruthenate as a catalyst, Swern oxidation, and Dess-Martin oxidation. However, from the viewpoint that toxic chrome is required in a stoichiometric amount, N-methylmorpholine oxide used as a co-oxidizing agent for oxidation with the use of tetrapropylammonium perruthenate as a catalyst is expensive, malodorous dimethyl sulfide or toxic carbon monoxide is produced as a by-product during Swern oxidation, and the Dess-Martin reagent has a risk of explosion during the synthesis, or the like, there is a demand for a chemical synthesis technique that is more environmentally friendly and can be carried out at a low cost. An example of such a chemical synthesis method is a dehydrogenation oxidation reaction using a catalyst. According to the reaction of method, it is unnecessary to use a toxic metal in a stoichiometric amount and an expensive co-oxidizing agent, and there are no problems of having malodor and risks originating from a by-product. As an example of the reaction, Oppenauer oxidation which uses aluminum isopropoxide as a catalyst and acetone or the like as a hydrogen acceptor is known. However, this reaction is disadvantageous in that the catalyst efficiency is not good and, although oxidation of secondary alcohols into ketones can be easily carried out, an application to other dehydrogenation oxidation reaction is difficult to achieve. As such, there is a demand for a catalytic reaction with high efficiency.

Examples of the catalyst having good efficiency include a ruthenium complex.

Examples of the method of producing a carbonyl compound by using a ruthenium complex as a dehydrogenation oxidation catalyst include the production of aldehydes from primary alcohols, the production of ketones from secondary alcohols, the production of esters from two molecules of alcohols, the production of esters from aldehydes and alcohols, the production of lactones from diols, the production of amides from alcohols and amines, the production of amides from aldehydes and amines, and the production of lactams from aminoalcohols.

As a method of producing aldehydes from primary alcohols that are represented by the following reaction general formula (1) by using a ruthenium complex as a dehydrogenation oxidation catalyst,

[Chem. 1]

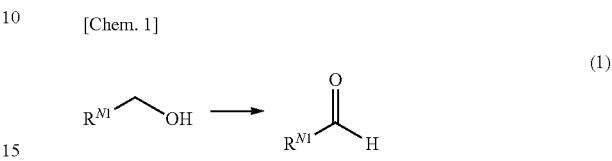

(in the formula, $R^{N1}$ represents a hydrogen atom or a monovalent organic group).

a method of using the ruthenium-μ-oxo-μ-hydroxo complex represented by the following chemical formula (2) which is described in Non Patent Literature 11

[Chem. 2]

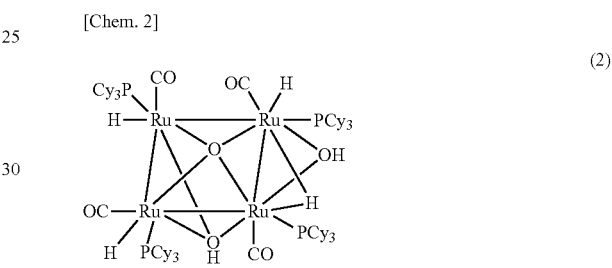

(in the formula, Cy represents a cyclohexyl group)

or the heterobimetallic rhodium-ruthenium complex represented by the following chemical formula (3) which is described in Non Patent Literature 14 is known.

[Chem. 3]

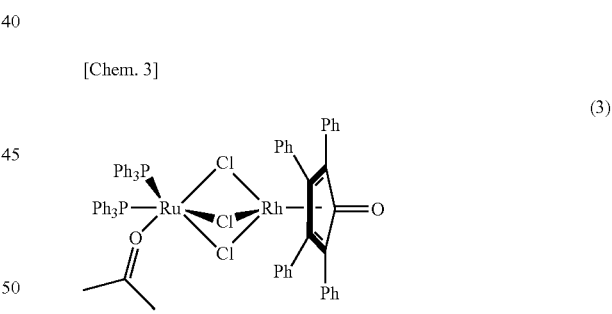

(in the formula, Ph represents a phenyl group)

However, with respect to the ruthenium-μ-oxo-μ-hydroxo complex disclosed in Non Patent Literature 11, only benzyl alcohols or aryl alcohols were used as a primary alcohol, which is a reacting compound. Further, as a primary alcohol that can be used for production of an aldehyde with good yield with the use of the heterobimetallic rhodium-ruthenium complex disclosed in Non Patent Literature 14, benzyl alcohols can be mentioned. However, it is also reported that the yield is lowered when 1-alkanol is used.

Further, to obtain conversion ratio at sufficient level, 2.5 mol % of the catalyst (as being a tetranuclear complex, it is 10 mol % in terms of ruthenium) is required for the ruthenium-μ-oxo-μ-hydroxo complex disclosed in Non Patent Literature 11, and the hetero bimetallic rhodium-ruthenium complex containing expensive rhodium is used in an amount of 0.5 mol % according to the method disclosed in Non Patent Literature 14.

Further, as a method of producing ketones from secondary alcohols that are represented by the following reaction general formula (4) by using a ruthenium complex as a dehydrogenation oxidation catalyst

[Chem. 4]

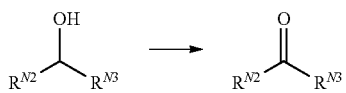

(4)

(in the formula, $R^{N2}$ and $R^{N3}$ each independently represent a hydrogen atom or a monovalent organic group), a method of using the ruthenium-diphosphine-diamine complex represented by the following chemical formula (5) which is disclosed in Non Patent Literature 1,

[Chem. 5]

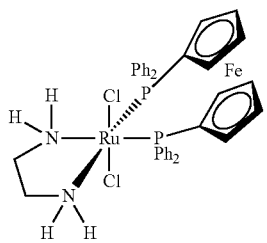

(5)

(in the formula, Ph represents a phenyl group)
a catalyst using the carbonyl tris(triphenylphosphine) ruthenium (II) dihydride disclosed in Non Patent Literature 10 in combination with diphosphine, the ruthenium-μ-oxo-μ-hydroxo complex represented by above chemical formula (2) which is disclosed in Non Patent Literature 11, the ruthenium-ferrocenyl oxazolinyl phosphine complex represented by the following chemical formula (6) which is disclosed in Non Patent Literature 15,

[Chem. 6]

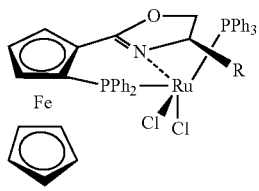

(6)

(in the formula, R represents an isopropyl group or a phenyl group)
the ruthenium-arene-diamine complex represented by the following chemical formula (7) which is disclosed in Non Patent Literature 16,

[Chem. 7]

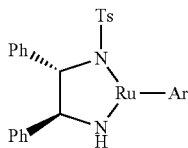

(7)

(in the formula, Ts represents a p-toluene sulfonyl group, Ar represents p-cymene or mesitylene, and Ph represents a phenyl group)
the binuclear ruthenium complex represented by the following chemical formula (8) which is disclosed in Non Patent Literature 17,

[Chem. 8]

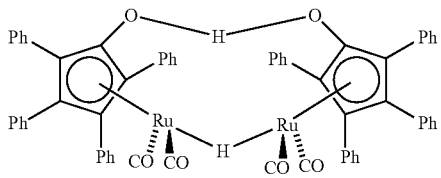

(8)

(in the formula, Ph represents a phenyl group)
or the tris(triphenylphosphine)ruthenium (II) dichloride complex which is disclosed in Non Patent Literature 18 is known.

However, with respect to the ruthenium-diphosphine-diamine complex disclosed in Non Patent Literature 1, the oxidation yield of acetophenone is only 58% after 20 hours even when 0.4 mol % of catalyst is used.

Further, the catalyst disclosed in Non Patent Literature 10 in which the carbonyl tris(triphenylphosphine) ruthenium (II) dihydride and diphosphine are used in combination requires the use of 1.25 to 2.5 mol % of catalyst and 24 hours of reaction time.

Further, although it is described that the ruthenium-μ-oxo-μ-hydroxo complex described in Non Patent Literature 11 has the same catalytic activity even after being re-used five times, since 2.5 mol % of the complex is used for single reaction (as being a tetranuclear complex, it is 10 mol % in terms of ruthenium), 0.5 mol % of the catalyst (as being a tetranuclear complex, 2 mol % in terms of ruthenium) is required when it is re-used five times.

Further, the ruthenium-ferrocenyl oxazolinyl phosphine complex disclosed in Non Patent Literature 15 requires a multi-step for synthesis of a ligand as described in Synlett., 1995, p 74-76 or Synlett., 1995, p 79-80, and therefore it is cumbersome to carry out and has poor yield.

Further, the ruthenium-arene-diamine complex disclosed in Non Patent Literature 16 requires the use of an optically active and expensive diamine ligand and the catalyst is required in amount of 0.2 mol %.

The binuclear ruthenium complex disclosed in Non Patent Literature 17 requires at least 20 hours of reaction time for many substrates when the catalyst is used in an amount of 0.1 mol %. Further, when cyclohexanol is used as a substrate, for example, the yield was only 60% after 24 hours.

The tris(triphenylphosphine)ruthenium (II) dichloride complex disclosed in Non Patent Literature 17 requires acetophenone as an additive for oxidation of 2-octanol, for example. Further, the yield was only 60% or so after 12 hours of reaction. Further, although a method of using the tris(triphenylphosphine)ruthenium (II) dichloride complex is also disclosed in Non Patent Literature 18, the yield was 71% after 24 hours of reaction when it was used in an amount of 0.2 mol %.

Further, as a method of producing esters from two alcohol molecules that are represented by the following reaction general formula (9) by using a ruthenium complex as a dehydrogenation oxidation catalyst

[Chem. 9]

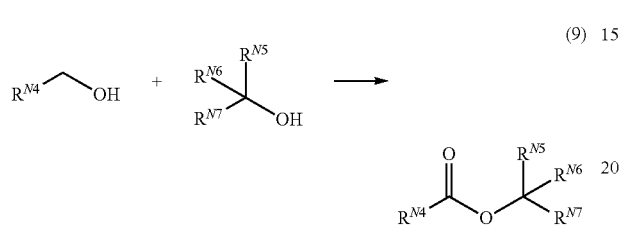
(9)

(in the formula, $R^{N4}$, $R^{N5}$, $R^{N6}$, and $R^{N7}$ each independently represent a hydrogen atom or a monovalent organic group), a method of using the ruthenium-carbonyl complex represented by the following chemical formula (10) which is disclosed in Non Patent Literature 6,

[Chem. 10]

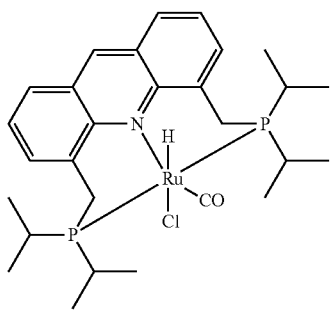
(10)

the ruthenium-carbonyl complex represented by the following chemical formula (11), chemical formula (12), or chemical formula (13) that are disclosed in Non Patent Literature 13

[Chem. 11]

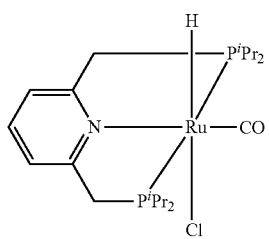
(11)

(in the formula, iPr represents an isopropyl group)

[Chem. 12]

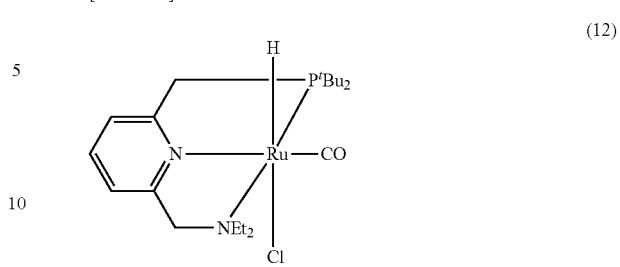
(12)

(in the formula, tBu represents a tert-butyl group and Et represents an ethyl group)

[Chem. 13]

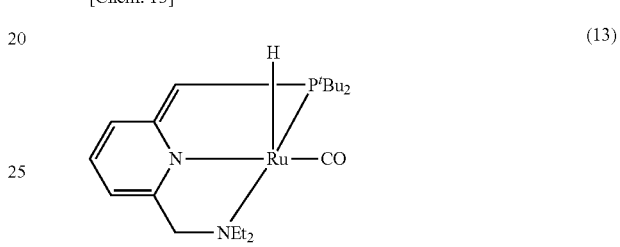
(13)

(in the formula, tBu represents a tert-butyl group and Et represents an ethyl group)

or the tetrakis(triphenylphosphine) ruthenium (II) dihydride complex which is disclosed in Non Patent Literature 19 is known.

However, with the ruthenium-carbonyl complex disclosed in Non Patent Literature 6, 26 to 72 hours of reaction time was required to have sufficient yield.

Further, to synthesize a ligand for the ruthenium-carbonyl complex represented by the chemical formula (11) which is disclosed in Non Patent Literature 13, extremely low temperature like −90 degrees C. is required as described in Organometallics, 2003, 22, p. 4604-4609, for example. To synthesize a ligand for the complex represented by the chemical formula (12) and the chemical formula (13), environmentally unfriendly carbon tetrachloride or extremely low temperature like −78 degrees C. is required.

Further, as a method of producing esters from aldehydes and alcohols that are represented by the following reaction general formula (14) by using a ruthenium complex as a dehydrogenation oxidation catalyst

[Chem. 14]

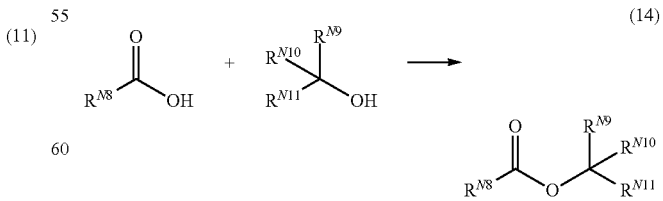
(14)

(in the formula, $R^{N8}$, $R^{N9}$, $R^{N10}$, and $R^{N11}$ each independently represent a hydrogen atom or a monovalent organic group), a method of using the ruthenium-carbonyl complex represented by above chemical formula (13) which is disclosed in Non Patent Literature 13 or the tetrakis(triphenylphosphine) ruthenium (II) dihydride complex which is disclosed in Non Patent Literature 19 is known.

However, to synthesize a ligand for the ruthenium carbonyl complex having a pyridine ring, one phosphino group, and one tertiary amine group as described in Non Patent Literature 13, environmentally unfriendly carbon tetrachloride or extremely low temperature like −78 degrees C. is required.

Further, according to the method of using the tetrakis (triphenylphosphine) ruthenium (II) dihydride complex which is disclosed in Non Patent Literature 19, it is required to have 24 hours of reaction time with the use of a catalyst in an amount of 5 mol %.

Further, regarding a method of producing lactones from diols that are represented by the following reaction general formula (15) by using a ruthenium complex as a dehydrogenation oxidation catalyst,

[Chem. 15]

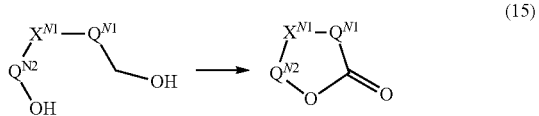
(15)

(in the formula, $Q^{N1}$-$X^{N1}$-$Q^{N2}$ represents a divalent organic group), they can be produced with high efficiency by using the ruthenium-phosphine-diamine complex represented by the following general formula (16) which is disclosed in Non Patent Literature 12.

[Chem. 16]

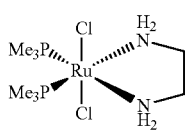
(16)

(in the formula, Me represents a methyl group).

Further, a method of using the tetrakis(triphenylphosphine) ruthenium (II) dihydride complex which is described in Non Patent Literature 19 or a method of using the Cp*RuCl (Ph$_2$P(CH$_2$)NH$_2$) complex which is described in Non Patent Literature 20 is known.

However, according to the method of using the ruthenium-phosphine-diamine complex which is disclosed in Non Patent Literature 12, it is required to have 48 hours under high temperature condition like 200 degrees C. or more to complete the reaction by using it in an amount of 0.0058 mol %.

Further, according to the method of using the tetrakis (triphenylphosphine) ruthenium (II) dihydride complex which is disclosed in Non Patent Literature 19, it is required to use 2 mol % of the catalyst.

Further, according to the method of using Cp*Ru(PN) complex which is disclosed in Non Patent Literature 20, it is required to use 1 mol % of the catalyst.

Further, as a method of producing amides from amines and alcohols that are represented by the following reaction general formula (17) by using a ruthenium complex as a dehydrogenation oxidation catalyst,

[Chem. 17]

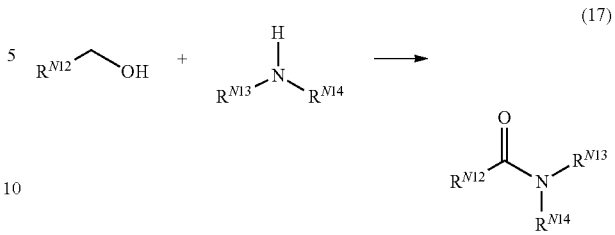
(17)

(in the formula, $R^{N12}$, $R^{N13}$, and $R^{N14}$ each independently represent a hydrogen atom or a monovalent organic group) (1) a method of using the ruthenium N-heterocyclic carbene complex as disclosed in Non Patent Literature 3, (2) a method of using the tetrakis(triphenylphosphine) ruthenium dihydride complex, N-heterocyclic carbene precursor, sodium hydride, and acetonitrile as disclosed in Non Patent Literature 4, (3) a method of using the ruthenium N-heterocyclic carbene complex as disclosed in Non Patent Literature 5, (4) a method of using arene ruthenium (II) chloride dimer complex, N-heterocyclic carbene precursor, sodium hydride, and acetonitrile or pyridine as disclosed in Non Patent Literature 7, (5) a method of using the dichloro(1,5-cyclooctadiene) ruthenium (II), N-heterocyclic carbene precursor, potassium tert-butoxide, and phosphine ligand as disclosed in Non Patent Literature 8, and (6) a method of using the ruthenium carbonyl complex having a pyridine ring, one phosphino group, and one tertiary amino group that is represented by above chemical formula (13) as disclosed in Non Patent Literature 9 are known.

However, the method disclosed in Non Patent Literature 3, 4, 5, 7, and 8 requires the use of 5 mol % catalyst.

Further, to synthesize a ligand for the ruthenium carbonyl complex having a pyridine ring, one phosphino group, and one tertiary amino group as disclosed in Non Patent Literature 9, environmentally unfriendly carbon tetrachloride or extremely low temperature like −78 degrees C. is required.

Further, as a method of producing amides from amines and aldehydes that are represented by the following reaction general formula (18) by using a ruthenium complex as a dehydrogenation oxidation catalyst,

[Chem. 18]

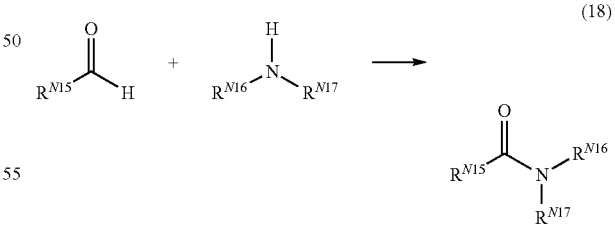
(18)

(in the formula, $R^{N15}$, $R^{N16}$, and $R^{N17}$ each independently represent a hydrogen atom or a monovalent organic group) (1) a method of using the tetrakis(triphenylphosphine) ruthenium dihydride complex, N-heterocyclic carbene precursor, sodium hydride, and acetonitrile as disclosed in Non Patent Literature 4, (2) a method of adding the ruthenium N-heterocyclic carbene complex and 10 mol % of primary alcohol as disclosed in Non Patent Literature 5, and (3) a method of using arene ruthenium (II) chloride dimer complex, N-heterocyclic carbene precursor, sodium hydride, and acetonitrile or pyridine as disclosed in Non Patent Literature 7 are known.

However, according to a method of using the tetrakis(triphenylphosphine) ruthenium dihydride complex, N-heterocyclic carbene precursor, sodium hydride, and acetonitrile as disclosed in Non Patent Literature 4, the method of adding the ruthenium N-heterocyclic carbene complex and 10 mol % of primary alcohol as disclosed in Non Patent Literature 5, or the method of using ruthenium, N-heterocyclic carbene precursor, a base, and acetonitrile or pyridine as disclosed in Non Patent Literature 7, 5 mol % of the catalyst and the reaction time of 24 to 36 hours are required.

Further, as a method of producing amides from aminoalcohols that are represented by the following reaction general formula (19) by using a ruthenium complex as a dehydrogenation oxidation catalyst

[Chem. 19]

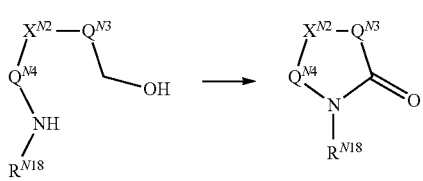
(19)

(in the formula, $R^{N18}$ represents a hydrogen atom or a monovalent organic group, the $Q^{N3}$-$X^{N2}$-$Q^{N4}$ represents a divalent organic group), a method of using the ruthenium-diphosphine-diamine complex represented by the following chemical formula (20) which is disclosed in Non Patent Literature 2,

[Chem. 20]

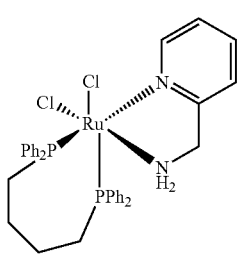
(20)

(in the formula, Ph represents a phenyl group), a method of using the ruthenium N-heterocyclic carbene complex which is disclosed in Non Patent Literature 3, and a method of using the ruthenium N-heterocyclic carbene complex which is disclosed in Non Patent Literature 5 are known.

However, with respect to the ruthenium-diphosphine-diamine catalyst which is disclosed in Non Patent Literature 2, the catalyst is required in an amount of 2.5 mol % to obtain sufficient conversion ratio.

Further, with respect to the ruthenium N-heterocyclic carbene complex which is disclosed in Non Patent Literature 3 and Non Patent Literature 5, the catalyst is required in an amount of 5 mol %.

CITATION LIST

Non Patent Literature

NPL 1: Chem. Eur. J. 2011, 17, p. 3474-3481.
NPL 2: Organometallics 2011, 2010, 29, p. 6548-6558.
NPL 3: Chem. Eur. J. 2010, 16, p. 6820-6827.
NPL 4: J. Org. Chem. 2010, 75, p. 3002-3006.
NPL 5: Organometallics 2010, 29, p. 1374-1378.
NPL 6: J. Am. Chem. Soc. 2009, 131, p. 3146-3147.
NPL 7: Adv. Synth. Catal. 2009, 351, p. 2643-2649.
NPL 8: J. Am. Chem. Soc. 2008, 130, p. 17672-17673.
NPL 9: Science 2007, 317, p. 790-792.
NPL 10: Tetrahedron Lett. 2007, 48, p. 3639-3641.
NPL 11: Organometallics 2006, 25, p. 1047-1051.
NPL 12: Organometallics 2005, 24, p. 2441-2446.
NPL 13: J. Am. Chem. Soc. 2005, 127, p. 10840-10841.
NPL 14: Organometallics 2004, 23, p. 3769-3771.
NPL 15: J. Org. Chem. 2003, 68, p. 5875-5880.
NPL 16: Angew. Chem. Int. Ed. 1997, 36, p. 288-290.
NPL 17: Chem. Eur. J. 1996, 2, p. 1533-1536.
NPL 18: J. Chem. Soc., Chem. Commun., 1992, p. 337-339.
NPL 19: J. Org. Chem. 1987, 52, p. 4319-4327.
NPL 20: Org. Lett. 2007, 9, p. 1821-1824.

SUMMARY OF INVENTION

Technical Problem

An object of the present invention is to provide a method for producing a compound having a carbonyl group by using a ruthenium complex that is easily prepared, easy to handle, and obtainable at a relatively low cost, as a dehydrogenation oxidation catalyst.

Solution to Problem

In view of the above circumstances, the present inventors have extensively studied, and as a result, have found that a carbonyl compound can be produced with the use of, as a dehydrogenation oxidation catalyst, a ruthenium complex having a tridentate ligand containing two phosphino groups and a —NH— group and a carbonyl ligand. This finding has led to the completion of the invention.

The present invention relates to the following [1] to [21].

[1] A method for producing a compound having a carbonyl group by dehydrogenation oxidation of a reacting compound in the presence of a dehydrogenation oxidation catalyst which contains the ruthenium carbonyl complex represented by the following general formula (21):

RuXY(CO)(L) (21)

wherein X and Y may be the same or different from each other and each represents an anionic ligand and L represents a tridentate aminodiphosphine ligand represented by the following general formula (22):

[Chem. 21]

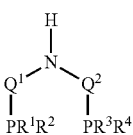
(22)

wherein $R^1$, $R^2$, $R^3$, and $R^4$ may be the same or different from one another and each represents a hydrogen atom, an alkyl group, a cycloalkyl group, an aryl group, an aralkyl group, an alkyloxy group, a cycloalkyloxy group, an aryloxy group, an aralkyloxy group, a heterocyclic group, or a substituted amino group, the $R^1$ and $R^2$ and/or $R^3$ and $R^4$ may be linked together to form a ring with an adjacent phosphorus atom, the alkyl group, the cycloalkyl group, the aryl group, the aralkyl group, the alkyloxy group, the cycloalkyloxy group, the aryloxy group, the aralkyloxy group, the heterocyclic group, and the substituted amino group may have one or more than one substituent, $Q^1$ and $Q^2$ may be the same or different from each other and each represents a divalent alkylene group that may have one or more than one substituent, a divalent cycloalkylene group that may have one or more than one substituent, or a divalent aralkylene group that may have one or more than one substituent.

[2] The production method described in above [1], wherein the tridentate aminodiphosphine ligand L of the ruthenium carbonyl complex is a tridentate aminodiphosphine ligand represented by the following general formula (23):

[Chem. 22]

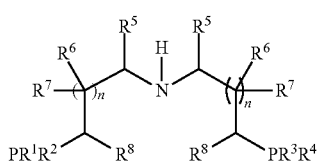

(23)

(in the formula, $R^1$, $R^2$, $R^3$, and $R^4$ represent the same groups as described above. wherein $R^5$, $R^6$, $R^7$, and $R^8$ may be the same or different from one another and each represents a hydrogen atom, an alkyl group that may have one or more than one substituent, a cycloalkyl group that may have one or more than one substituent, an aryl group that may have one or more than one substituent, or an aralkyl group that may have one or more than one substituent, and n is an integer of 0 to 3.)

[3] The method according to the above [1] or [2], wherein the tridentate aminodiphosphine ligand L of the ruthenium carbonyl complex is represented by the following general formula (24):

[Chem. 23]

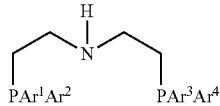

(24)

wherein $Ar^1$, $Ar^2$, $Ar^3$, and $Ar^4$ may be the same or different from one another and each represents an aryl group or an aromatic heterocyclic group, and these aryl group and aromatic heterocyclic group may have one or more than one substituent.

[4] The method according to the above [3], wherein $Ar^1$, $Ar^2$, $Ar^3$, and $Ar^4$ in the general formula (24) are each a phenyl group that may have one or more than one substituent.

[5] The method according to the above [4], wherein the tridentate aminodiphosphine ligand L of the ruthenium carbonyl complex is represented by the following general formula (25):

[Chem. 24]

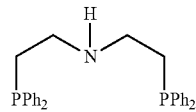

(25)

wherein Ph represents a phenyl group.

[6] The method according to the above [1] or [2], wherein the tridentate aminodiphosphine ligand L of the ruthenium carbonyl complex is an optically active tridentate aminodiphosphine ligand.

[7] The method according to any one of the above [1] to [6], wherein anionic ligand represented by X in the general formula (21) is a hydride and anionic ligand represented by Y in the general formula (21) is Cl.

[8] The method according to any one of the above [1] to [6], wherein anionic ligand represented by X in the general formula (21) is a hydride and anionic ligand represented by Y in the general formula (21) is $BH_4$.

[9] The production method described in any one of the above [1] to [8], in which the dehydrogenation oxidation reaction is carried out in the presence of a base.

[10] The production method described in any one of the above [1] to [9]), in which the compound having a carbonyl group is a compound selected from a group consisting of aldehydes, ketones, esters, amide, lactones, and lactams.

[11] The production method described in any one of the above [1] to [10], in which the compound having a carbonyl group is a compound having a carbonyl group which is represented by the following general formula (Z)

$$R^{P1}\text{—CO—}Y^K\text{—}R^{P2} \qquad (Z)$$

(in the formula, $R^{P1}$ and $R^{P2}$ may be the same or different from each other and each represents a hydrogen atom, an alkyl group, a cycloalkyl group, an aryl group, an aralkyl group, a heterocyclic group, an alkenyl group, an alkynyl group, a cycloalkenyl group, an alkoxycarbonyl group, a cycloalkyloxycarbonyl group, an aryloxycarbonyl group, an aralkyloxycarbonyl group, an alkenyloxycarbonyl group, an alkynyloxycarbonyl group, a cycloalkenyloxycarbonyl group, a carboxamide group, a phosphono group, a phosphinoyl group, a phosphoryl group, a sulfonyl group, a sulfo group, an alkyloxy group, a cycloalkyloxy group, an aryloxy group, an aralkyloxy group, an alkenyloxy group, an alkynyloxy group, a cycloalkenyloxy group, or a hydroxy group which may be protected, and the alkyl group, the cycloalkyl group, the aryl group, the aralkyl group, the heterocyclic group, the alkenyl group, the alkynyl group, the cycloalkenyl group, the alkoxycarbonyl group, the cycloalkyloxycarbonyl group, the aryloxycarbonyl group, the aralkyloxycarbonyl group, the alkenyloxycarbonyl group, the alkynyloxycarbonyl group, the cycloalkenyloxycarbonyl group, the carboxamide group, the phosphono group, the phosphinoyl group, the phosphoryl group, the sulfonyl group, the sulfo group, the alkyloxy group, the cycloalkyl oxy group, the aryloxy group, the aralkyloxy group, the alkenyloxy group, the alkynyloxy group, and the cycloalkenyloxy group may have a substituent group.

Further, $R^{P1}$ and $R^{P2}$ together may form a divalent alkylene group, a divalent cycloalkylene group, a divalent allylene group, or a divalent aralkylene group, and the divalent alkylene group, the divalent cycloalkylene group, the divalent allylene group, or the divalent aralkylene group may have a substituent group, and at least one carbon atom of the divalent group may be substituted with an oxygen atom, a sulfur atom, or N—$R^Z$ (in the formula, $R^Z$ represents the same group as $R^{P1}$ above or a protective group for an amino group).

$Y^K$ represents a bonding arm, an oxygen atom, N—$R^Z$ (in the formula, $R^Z$ represents the same group as $R^{P1}$ above or a protective group for an amino group), or —O—C($R^{T1}$)($R^{T2}$)— (in the formula, $R^{T1}$ and $R^{T2}$ may be the same or different from each other and represents the same group as $R^{P1}$ above)).

[12] The production method described in above [11], in which $R^{P1}$, $R^{P2}$, $R^{T1}$, $R^{T2}$, and $R^Z$ in the general formula (Z) above each independently represents a hydrogen atom, an alkyl group which may have a substituent group, a cycloalkyl group which may have a substituent group, an aryl group which may have a substituent group, an aralkyl group which may have a substituent group, a heterocyclic group which may have a substituent group, an alkenyl group which may have a substituent group, an alkynyl group which may have a substituent group, or a cycloalkenyl group which may have a substituent group, or $R^{P1}$ and $R^{P2}$ together form a divalent alkylene group which may have a substituent group, a divalent cycloalkylene group which may have a substituent group, a divalent allylene group which may have a substituent group, or a divalent aralkylene group which may have a substituent group.

[13] The production method described in any one of the above [1] to [12], in which the reacting compound is a primary alcohol represented by the following general formula (26)

[Chem. 25]

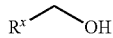

(26)

(in the formula, $R^X$ represents a hydrogen atom, an alkyl group, a cycloalkyl group, an aryl group, an aralkyl group, a heterocyclic group, an alkenyl group, an alkynyl group, a cycloalkenyl group, an oxycarbonyl group, a carboxamide group, a phosphono group, a phosphoryl group, a sulfonyl group, or a sulfo group, and the alkyl group, the cycloalkyl group, the aryl group, the aralkyl group, the heterocyclic group, the alkenyl group, the alkynyl group, the cycloalkenyl group, the oxycarbonyl group, the carboxamide group, the phosphono group, the phosphoryl group, the sulfonyl group, or the sulfo group may have a substituent group), and the compound having a carbonyl group to be produced is aldehydes represented by the following general formula (27).

[Chem. 26]

(27)

[14] The production method described in any one of the above [1] to [12], in which the reacting compound is a secondary alcohol represented by the following general formula (28)

[Chem. 27]

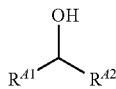

(28)

(in the formula, $R^{A1}$ and $R^{A2}$ may be the same or different from each other and represent the same group as $R^X$ in the general formula (26), an alkyloxy group, a cycloalkyloxy group, an aryloxy group, an aralkyloxy group, an alkenyloxy group, an alkynyloxy group, a cycloalkenyloxy group, or a hydroxy group which may be protected, and the alkyl group, the cycloalkyl group, the aryl group, the aralkyl group, the heterocyclic group, the alkenyl group, the alkynyl group, the cycloalkenyl group, the alkoxycarbonyl group, the cycloalkyloxycarbonyl group, the aryloxycarbonyl group, the aralkyloxycarbonyl group, the alkenyloxycarbonyl group, the alkynyloxycarbonyl group, the cycloalkenyloxycarbonyl group, the carboxamide group, the phosphono group, the phosphinoyl group, the phosphoryl group, the sulfonyl group, the sulfo group, the alkyloxy group, the cycloalkyloxy group, the aryloxy group, the aralkyloxy group, the alkenyloxy group, the alkynyloxy group, and the cycloalkenyloxy group may have a substituent group. Further, $R^{A1}$ and $R^{A2}$ may be linked to each other to form a ring), and the compound having a carbonyl group to be produced is ketones represented by the following general formula (29).

[Chem. 28]

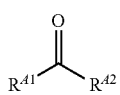

(29)

(in the formula, $R^{A1}$ and $R^{A2}$ are as defined in above).

[15] The production method described in any one of the above [1] to [12], in which the reacting compound is alcohols represented by the following general formula (30)

[Chem. 29]

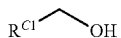

(30)

(in the formula, $R^{C1}$ represents the same group as $R^X$ which is explained above in relation to the general formula (26)) and alcohols represented by the following general formula (31),

[Chem. 30]

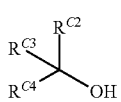

(31)

(in the formula, $R^{C2}$, $R^{C3}$, and $R^{C4}$ may be the same or different from one another and represent the same group as $R^X$ which is explained above in relation to the general formula (26). Further, $R^{C2}$ and $R^{C3}$ and/or $R^{C4}$ may be linked together to form a ring), and the compound having a carbonyl group to be produced is esters represented by the following general formula (32)

[Chem. 31]

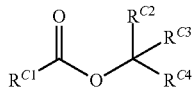
(32)

(in the formula, $R^{C1}$, $R^{C2}$, $R^{C3}$, and $R^{C4}$ are as defined above).

[16] The production method described in any one of the above [1] to [12], in which the reacting compound is aldehydes represented by the following general formula (33),

[Chem. 32]

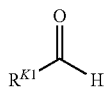
(33)

(in the formula, $R^{K1}$ represents a hydrogen atom or the same group as $R^{A1}$ and $R^{A2}$ which are explained above in relation to the general formula (28)), and alcohols represented by the following general formula (34),

[Chem. 33]

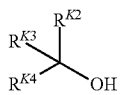
(34)

(in the formula, $R^{K2}$, $R^{K3}$, and $R^{K4}$ may be the same or different from one another and represent the same group as $R^X$ which is explained above in relation to the general formula (26). Further, $R^{K2}$ and $R^{K3}$ and/or $R^{K4}$ may be linked together to form a ring), and the compound having a carbonyl group to be produced is esters represented by the following general formula (35)

[Chem. 34]

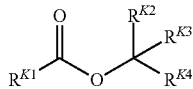
(35)

(in the formula, $R^{K1}$, $R^{K2}$, $R^{K3}$, and $R^{K4}$ are as defined above).

[17] The production method described in any one of the above [1] to [12], in which the reacting compound is diols represented by the following general formula (36),

[Chem. 35]

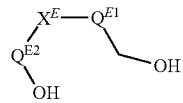
(36)

(in the formula, $Q^{E1}$ and $Q^{E2}$ may be the same or different from each other and each represents a bonding arm, a divalent alkylene group, a divalent cycloalkylene group, a divalent allylene group, or a divalent aralkylene group, and the divalent alkylene group, the divalent cycloalkylene group, the divalent allylene group, or the divalent aralkylene group may have a substituent group. $X^E$ represents a bonding arm (with the proviso that $Q^{E1}$, $Q^{E2}$, and $X^E$ do not simultaneously represent a bonding arm), an oxygen atom, a sulfur atom, or N—$R^E$ ($R^E$ represents the same group as $R^{K1}$ which is explained above in relation to the general formula (33), or a protective group that is described as a protective group for an amino group in Reference Literature 1 (Protective Groups in Organic Synthesis Second Edition, JOHN WILEY & SONS, INC. 1991) described above. The descriptions of Reference Literature 1 are incorporated herein as a reference), and the compound having a carbonyl group to be produced is lactones represented by the following general formula (37)

[Chem. 36]

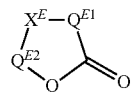
(37)

(in the formula, $Q^{E1}$, $Q^{E2}$, and $X^E$ represent the same groups as described above.)

[18] The production method described in any one of the above [1] to [12], in which the reacting compound is alcohols represented by the following general formula (38)

[Chem. 37]

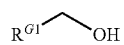
(38)

(in the formula, $R^{G1}$ represents the same group as $R^X$ which is explained above in relation to the general formula (26)), and amines represented by the following general formula (39),

[Chem. 38]

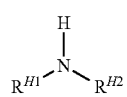
(39)

(in the formula, $R^{H1}$ and $R^{H2}$ may be the same or different from each other and each represents the same group as $R^E$ which is explained above in relation to N—$R^E$ of the general formula (36). Further, $R^{H1}$ and $R^{H2}$ may be linked together to form a ring), and the compound having a carbonyl group to be produced is amides represented by the following general formula (40)

[Chem. 39]

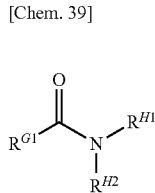

(40)

(in the formula, $R^{G1}$, $R^{H1}$, and $R^{H2}$ represent the same groups as described above.)

[19] The production method described in any one of the above [1] to [12], in which the reacting compound is aldehydes represented by the following general formula (41),

[Chem. 40]

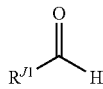

(41)

(in the formula, $R^{J1}$ represents the same group as $R^{K1}$ which is explained above in relation to the general formula (33)) and amines represented by the following general formula (42),

[Chem. 41]

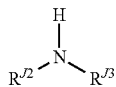

(42)

(in the formula, $R^{J2}$ and $R^{J3}$ may be the same or different from each other and each represents the same group as $R^E$ which is explained above in relation to N—$R^E$ of the general formula (36). Further, $R^{J2}$ and $R^{J3}$ may be linked together to form a ring), and the compound having a carbonyl group to be produced is amides represented by the following general formula (43)

[Chem. 42]

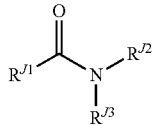

(43)

(in the formula, $R^{J1}$, $R^{J2}$, and $R^{J3}$ represent the same groups as described above.).

[20] The production method described in any one of the above [1] to [12], in which the reacting compound is aminoalcohols represented by the following general formula (44),

[Chem. 43]

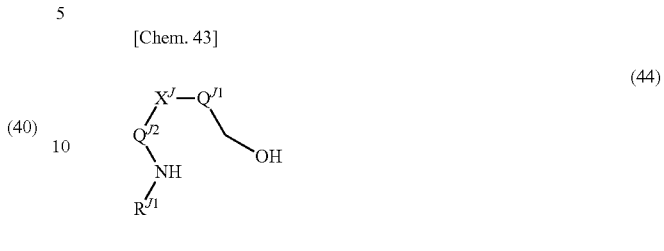

(44)

(in the formula, $Q^{J1}$ and $Q^{J2}$ may be the same or different from each other and each represents the same group as $Q^{E1}$ and $Q^{E2}$ which are explained above in relation to the general formula (36). Further, $X^J$ represents the same group as $X^E$ which is explained above in relation to the general formula (36) (with the proviso that $Q^{J1}$, $Q^{J2}$, and $X^J$ do not simultaneously represent a bonding arm)), and the compound having a carbonyl group to be produced is lactams represented by the following general formula (45)

[Chem. 44]

(45)

(in the formula, $Q^{J1}$, $Q^{J2}$, $X^J$, and $R^{J1}$ represent the same groups as described above.)

[21] A dehydrogenation oxidation catalyst consisting of the ruthenium carbonyl complex that is described in any one of the above (1) to (8).

Advantageous Effects of Invention

The ruthenium carbonyl complex used in the present invention can be easily produced from a tridentate aminodiphosphine ligand and a ruthenium carbonyl complex as a precursor. The tridentate aminodiphosphine ligand can be easily produced by reacting a bisalkylamine having elimination groups with a phosphine compound in the presence of a base. Further, the ruthenium carbonyl complex as a precursor can be easily produced from an easily available inorganic ruthenium compound. Such a ruthenium carbonyl complex of the present invention is not only easily produced but also highly stable and easy to handle, and is therefore suitable for use in industrial applications.

The ruthenium carbonyl complex that is used in the invention has high catalytic activity as a dehydrogenation oxidation catalyst even under relatively mild reaction conditions. Further, the dehydrogenation oxidation reaction using the complex can be also carried out in the presence or absence of a hydrogen acceptor, depending on a specific case. Further, by adding a base, if necessary, the dehydrogenation oxidation reaction can be carried out with higher efficiency.

Further, the ruthenium carbonyl complex of the invention has an excellent catalytic activity for an intramolecular or intermolecular dehydrogenation oxidation reaction, and makes it possible to efficiently produce at a low cost not only aldehydes and ketones but also esters, amides, lactones, and lactams.

DESCRIPTION OF EMBODIMENTS

First, a ruthenium carbonyl complex of the present invention will be described.

The ruthenium carbonyl complex is represented by the following general formula (21):

$$RuXY(CO)(L) \tag{21}$$

wherein X and Y may be the same or different each other and each represents an anionic ligand and L represents a tridentate aminodiphosphine ligand represented by the following general formula (22):

[Chem. 45]

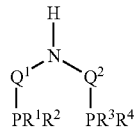

(22)

The tridentate aminodiphosphine ligand used in the present invention will be described. An example of the tridentate aminodiphosphine ligand represented by L in the general formula (21) has containing two phosphino groups and a —NH— group. A specific example of the tridentate aminodiphosphine ligand is the one represented by above general formula (22).

$R^1$, $R^2$, $R^3$, and $R^4$ in the general formula (22) will be described.

An example of alkyl group is a linear or branched alkyl group having 1 to 50 carbon atoms, preferably 1 to 20 carbon atoms, more preferably 1 to 10 carbon atoms. Specific examples thereof include a methyl group, an ethyl group, an n-propyl group, an isopropyl group, an n-butyl group, an isobutyl group, a sec-butyl group, a tert-butyl group, an n-pentyl group, an n-hexyl group, an n-octyl group, and the like.

An example of the cycloalkyl group is a monocyclic, polycyclic, or fused-ring cycloalkyl group having 3 to 30 carbon atoms, preferably 3 to 20 carbon atoms, more preferably 3 to 10 carbon atoms. Specific examples thereof include a cyclopropyl group, a cyclopentyl group, a cyclohexyl group, and the like.

An example of aryl group is a monocyclic, polycyclic, or fused-ring aryl group having 6 to 36 carbon atoms, preferably 6 to 18 carbon atoms, more preferably 6 to 14 carbon atoms. Specific examples thereof include a phenyl group, a naphthyl group, an anthryl group, a phenanthryl group, a biphenyl group, and the like.

An example of aralkyl group is a group obtained by substituting at least one hydrogen atom of the above-mentioned alkyl group with above-mentioned aryl group. For example, aralkyl group preferably has 7 to 15 carbon atoms. Specific examples thereof include a benzyl group, a 1-phenylethyl group, a 2-phenylethyl group, a 1-phenylpropyl group, a 3-naphthylpropyl group, and the like.

An example of alkyloxy group is an alkyloxy group having a liner or branched alkyl group having 1 to 20 carbon atoms, preferably 1 to 15 carbon atoms, more preferably 1 to 10 carbon atoms. Specific examples thereof include a methoxy group, an ethoxy group, an n-propoxy group, an isopropoxy group, an n-butoxy group, an isobutoxy group, an sec-butoxy group, a tert-butoxy group, an n-pentyloxy group, and the like.

An example of the cycloalkyloxy group is a cycloalkyloxy group having a monocyclic, polycyclic or fused-ring cycloalkyl group having 3 to 20 carbon atoms, preferably 3 to 15 carbon atoms, more preferably 3 to 10 carbon atoms. Specific examples thereof include a cyclopropyloxy group, a cyclopentyloxy group, a cyclohexyloxy group, and the like.

An example of aryloxy group is an aryloxy group having a monocyclic, polycyclic, or fused-ring aryl group having 6 to 36 carbon atoms, preferably 6 to 18 carbon atoms, more preferably 6 to 14 carbon atoms. Specific examples thereof include a phenoxy group, a tolyloxy group, a xylyloxy group, a naphthoxy group, and the like.

An example of aralkyloxy group is a group obtained by substituting at least one hydrogen atom of alkyl group of the above-mentioned alkyloxy group or of the above-mentioned cycloalkyl group with above-mentioned aryl group. For example, aralkyloxy group preferably has 7 to 15 carbon atoms. Specific examples thereof include a benzyloxy group, a 1-phenylethoxy group, a 2-phenylethoxy group, a 1-phenylpropoxy group, a 2-phenylpropoxy group, a 3-phenylpropoxy group, a 4-phenylbutoxy group, a 1-naphthylmethoxy group, a 2-naphthylmethoxy group, and the like.

Examples of the heterocyclic group include an aliphatic heterocyclic group and an aromatic heterocyclic group. An example of aliphatic heterocyclic group is a 3- to 8-membered (preferably 4- to 6-membered) monocyclic, polycyclic, or fused-ring aliphatic heterocyclic group having 2 to 14 carbon atoms and at least one heteroatom (preferably 1 to 3 heteroatoms) such as a nitrogen atom, an oxygen atom, and/or a sulfur atom. Specific examples of such an aliphatic heterocyclic group include an azetidyl group, an azetidino group, a pyrrolidyl group, a pyrrolidino group, a piperidinyl group, a piperidino group, a piperadinyl group, a piperadino group, a morpholinyl group, a morpholino group, a tetrahydrofuryl group, a tetrahydropyranyl group, a tetrahydrothiophenyl group, and the like.

An example of aromatic heterocyclic group is a 5- or 6-membered monocyclic, polycyclic, or fused-ring heteroaryl group having 2 to 15 carbon atoms and at last one heteroatom (preferably 1 to 3 heteroatoms) such as a nitrogen atom, an oxygen atom, and/or a sulfur atom. Specific examples thereof include a furyl group, a thienyl group, a pyridyl group, a pyrimidyl group, a pyrazyl group, a pyridazyl group, a pyrazolyl group, an imidazolyl group, an oxazolyl group, a thiazolyl group, a benzofuryl group, a benzothienyl group, a quinolyl group, an isoquinolyl group, a quinoxalyl group, a phthalazyl group, a quinazolyl group, a naphthyridyl group, a cinnolyl group, a benzoimidazolyl group, a benzoxazolyl group, a benzothiazolyl group, an acridyl group, an acridinyl group, and the like.

An example of the substituted amino group is an amino group obtained by substituting two hydrogen atoms of an amino group with above-mentioned alkyl, cycloalkyl, aryl, aralkyl, and/or heterocyclic groups which are the same or different from each other. Specific examples thereof include: a dialkylamino group such as an N,N-diethylamino group or an N,N-diisopropylamino group; a dicycloalkylamino group such as an N,N-dicyclohexylamino group; a diarylamino group such as an N,N-diphenylamino group or an N-naphthyl-N-phenylamino group; a diaralkylamino group such as an N,N-dibenzylamino group, and the like. Alkyl group, the cycloalkyl group, the aryl group, the aralkyl group, and the heterocyclic group as substituents of the substituted amino group may further have one or more than one substituent.

Examples of the substituents that may be possessed by the alkyl group, the cycloalkyl group, the aryl group, the aralkyl group, the alkyloxy group, the cycloalkyloxy group, the aryloxy group, the aralkyloxy group, the heterocyclic group, and the alkyl group, the cycloalkyl group, the aryl group, the aralkyl group, and the heterocyclic group on the substituted amino group include the above-mentioned alkyl group, cycloalkyl group, aryl group, aralkyl group, alkyloxy group, cycloalkyloxy group, aryloxy group, aralkyloxy group, heterocyclic group, substituted amino group, a halogen atom, a silyl group, an optionally-protected hydroxyl group, and the like.

Examples of the halogen atom as substituents of $R^1, R^2, R^3$, and $R^4$ include a fluorine atom, a chlorine atom, a bromine atom, and an iodine atom.

Examples of the silyl group as substituents of $R^1, R^2, R^3$, and $R^4$ include one obtained by replacing three hydrogen atoms of a silyl group with above-mentioned alkyl, cycloalkyl, aryl, and/or aralkyl groups, and the like. Specific examples thereof include a trimethylsilyl group, a triethylsilyl group, a tert-butyldimethylsilyl group, a tert-butyldiphenylsilyl group, a triphenylsilyl group, and the like.

Examples of the optionally-protected hydroxy group as substituents of $R^1$, $R^2$, $R^3$, and $R^4$ include a unprotected hydroxy group and hydroxy groups that may be protected by common protective groups for a hydroxy group for use in, for example, peptide synthesis which are described in, for example, Reference Document 1 (Protective Groups in Organic Synthesis Second Edition, JOHN WILEY & SONS, INC. 1991). Examples of such protective groups include a silyl group such as a trimethylsilyl group, a tert-butyldimethylsilyl group, and a tert-butyldiphenylsilyl group, a benzyl group, a methoxymethyl group, and the like.

$Q^1$ and $Q^2$ in the general formula (22) will be described.

An example of the divalent alkylene group is a linear or branched divalent alkyl chain having 1 to 20 carbon atoms, preferably 1 to 10 carbon atoms, more preferably 1 to 6 carbon atoms. Specific examples thereof include a methylene group, an ethylene group, a trimethylene group, a tetramethylene group, a pentamethylene group, and the like.

An example of the divalent cycloalkylene group is a divalent group having a monocyclic, polycyclic, or fused-ring cycloalkyl group having 3 to 15 carbon atoms, preferably 3 to 10 carbon atoms, more preferably 3 to 6 carbon atoms. Specific examples thereof include a cyclopropylene group, a cyclobutylene group, a cyclopenthylene group, a cyclohexylene group, and the like.

An example of the divalent aralkylene group is a divalent group having 7 to 11 carbon atoms, which is obtained by removing one hydrogen atom from an aryl group of an aralkyl group such as a benzyl group or a phenethyl group. Specific examples thereof include a benzylene group (-Ph-CH$_2$—), a 2-phenylethylene group (-Ph-CH$_2$CH$_2$—), a 1-naphthylmethylene group (—Np—CH$_2$—), a 2-naphthylmethylene group (—Np—CH$_2$—), and the like (in these general formulas, -Ph- represents a phenylene group and —Np— represents a naphthylene group).

Examples of the substituents that may be possessed by the divalent alkylene group, the divalent cycloalkylene group, or the divalent aralkylene group include alkyl group, the cycloalkyl group, the aryl group, the aralkyl group, the alkyloxy group, the cycloalkyloxy group, the aryloxy group, the aralkyloxy group, the heterocyclic group, the halogen atom, the silyl group, the substituted amino group, the optionally-protected hydroxy group, and the like, which have been described above with reference to $R^1, R^2, R^3$, and $R^4$ in the general formula (22).

Herein below, a monovalent anionic ligand represented by X or Y in the general formula (21) will be described.

Examples of the monovlaent anionic ligand include a hydride, an alkyloxy group, a cycloalkyloxy group, an aryloxy group, an aralkyloxy group, a hydroxy group, an acyloxy group, a sulfonyloxy group, a halogen ion, AlH$_4^-$, AlH$_2$(OCH$_2$CH$_2$OCH$_3$)$_2^-$, BH$_4^-$, BH$_3$H$_3$CN$^-$, BH(Et)$_3^-$, BH(sec-Bu)$_3^-$, and the like. Among them, BH$_4^-$, a hydride, and a chlorine ion are preferred. It is to be noted that, in this specification, a hydride is also sometimes simply referred to as "hydrogen" and a halogen ion is also sometimes simply referred to as "halogen".

An example of acyloxy group is the one represented by the following general formula (46).

[Chem. 46]

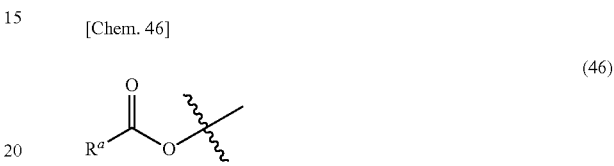

(46)

$R^a$ in the general formula (46) is a hydrogen atom, an alkyl group, a cycloalkyl group, an aryl group, and an aralkyl group. Examples of alkyl group, the cycloalkyl group, the aryl group, and aralkyl group include those described above with reference to $R^1, R^2, R^3$, and $R^4$ in the general formula (22). These alkyl group, the cycloalkyl group, the aryl group, and aralkyl group may further have one or more than one substituent, and examples of such substituents include alkyl group, the cycloalkyl group, the aryl group, the aralkyl group, the alkyloxy group, the cycloalkyloxy group, the aralkyloxy group, the aryloxy group, the heterocyclic group, the halogen atom, the silyl group, and the optionally-protected hydroxy group which have been described above with reference to $R^1$, $R^2$, $R^3$, and $R^4$ in the general formula (22), an optionally-protected amino group, and the like.

Examples of the optionally-protected amino group as substituents of $R^a$ include: an unprotected amino group; a mono- or dialkylamino group such as an N-methylamino group, an N,N-dimethylamino group, an N,N-diethylamino group, an N,N-diisopropylamino group, or an N-cyclohexylamino group; a mono- or diarylamino group such as an N-phenylamino group, an N,N-diphenylamino group, an N-naphthylamino group, or an N-naphthyl-N-phenylamino group; a mono- or diaralkylamino group such as an N-benzylamino group or an N, N-dibenzylamino group; an acylamino group such as a formylamino group, an acetylamino group, a propionylamino group, a pivaloylamino group, a pentanoylamino group, a hexanoylamino group, or a benzoylamino group; an alkoxycarbonylamino group such as a methoxycarbonylamino group, an ethoxycarbonylamino group, an n-propoxycarbonylamino group, an n-butoxycarbonylamino group, a tert-butoxycarbonylamino group, a pentyloxycarbonylamino group, or a hexyloxycarbonylamino group; an aryloxycarbonylamino group such as a phenyloxycarbonylamino group; an aralkyloxycarbonylamino group such as a benzyloxycarbonylamino group, and the like. Other examples of the optionally-protected amino group include amino groups protected by common protective groups for amino groups for use in, for example, peptide synthesis, and the like which are described in, for example, above-mentioned Reference Document 1.

Specific examples of $R^a$ include a methyl group, an ethyl group, a propyl group, a tert-butyl group, a trifluoromethyl group, a phenyl group, a pentafluorophenyl group, and the like.

An example of the sulfonyloxy group is the one represented by the following formula (47).

[Chem. 47]

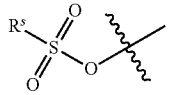
(47)

$R^s$ in the general formula (47) are the same as above-mentioned examples of $R^a$ in acyloxy group.

Examples of the halogen ion include a fluorine ion, a chlorine ion, a bromine ion, and an iodine ion. Among them, a chlorine ion and a bromine ion are preferred, and a chlorine ion is more preferred.

A preferred example of the tridentate aminophosphine ligand is the one represented by the following general formula (23).

[Chem. 48]

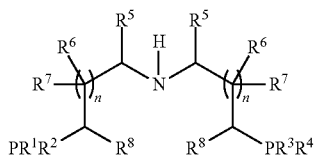
(23)

(in the formula, $R^1$, $R^2$, $R^3$, and $R^4$ represent the same groups as described above.
wherein $R^5$, $R^6$, $R^7$, and $R^8$ may be the same or different from one another and each represents a hydrogen atom, an alkyl group, a cycloalkyl group, an aryl group, or an aralkyl group.

n is an integer of 0 to 3; and these alkyl group, the cycloalkyl group, the aryl group, and aralkyl group may have one or more than one substituent.

Examples of alkyl group, the cycloalkyl group, the aryl group, and aralkyl group represented by $R^5$, $R^6$, $R^7$, and $R^8$ in the general formula (23) include those described above with reference to $R^1$, $R^2$, $R^3$, and $R^4$ in the general formula (22). Examples of the substituents that may be possessed by these alkyl group, the cycloalkyl group, the aryl group, and aralkyl group include alkyl group, the cycloalkyl group, the aryl group, the aralkyl group, the alkyloxy group, the cycloalkyloxy group, the aryloxy group, the aralkyloxy group, the heterocyclic group, the halogen atom, the silyl group, the substituted amino group, the optionally-protected hydroxy group, and the like, which have been described above with reference to $R^1$, $R^2$, $R^3$, and $R^4$ in the general formula (22).

A more preferred example of the tridentate aminodiphosphine ligand is the one represented by the following general formula (24).

[Chem. 49]

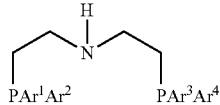
(24)

wherein $Ar^1$, $Ar^2$, $Ar^3$, and $Ar^4$ may be the same or different from one another and each represents an aryl group or an aromatic heterocyclic group, and these aryl group and aromatic heterocyclic group may have one or more than one substituent.

Examples of aryl group and aromatic heterocyclic group in the general formula (24) include aryl group, the aromatic heterocyclic group as an example of the heterocyclic group, and the like, which have been described above with reference to $R^1$, $R^2$, $R^3$, and $R^4$ in the general formula (22). Examples of the substituents that may be possessed by these aryl group and aromatic heterocyclic group include alkyl group, the cycloalkyl group, the aryl group, the aralkyl group, the alkyloxy group, the cycloalkyloxy group, the aryloxy group, the aralkyloxy group, the halogen atom, the silyl group, the heterocyclic group, the substituted amino group, the optionally-protected hydroxy group, and the like, which have been described above with reference to $R^1$, $R^2$, $R^3$, and $R^4$ in the general formula (22).

An even more preferred example of the tridentate aminodiphosphine ligand is the one represented by the following general formula (25).

[Chem. 50]

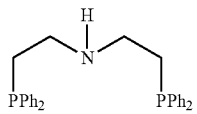
(25)

(wherein Ph represents a phenyl group.)

The tridentate aminodiphosphine ligand represented by the general formula (22) or (23) may be used as an optically active ligand of the ruthenium carbonyl complex represented by the general formula (21) depending on the substituents on $Q^1$ or $Q^2$ or $R^1$ to $R^8$.

A ruthenium compound as a starting material for producing a ruthenium carbonyl complex used in the present invention is not particularly limited, and examples thereof include inorganic ruthenium compounds such as a $RuCl_3$ hydrate, a $RuBr_3$ hydrate, and a $RuI_3$ hydrate, $RuCl_2(DMSO)_4$, [Ru(cod)$Cl_2]_n$, [Ru(nbd)$Cl_2]_n$, (cod)Ru(2-methallyl)$_2$, [Ru(benzene)$Cl_2]_2$, [Ru(benzene)$Br_2]_2$, [Ru(benzene)$I_2]_2$, [Ru(p-cymene)$Cl_2]_2$, [Ru(p-cymene)$Br_2]_2$, [Ru(p-cymene)$I_2]_2$, [Ru(mesitylene)$Cl_2]_2$, [Ru(mesitylene)$Br_2]_2$, [Ru(mesitylene)$I_2]_2$, [Ru(hexamethylbenzene)$Cl_2]_2$, [Ru(hexamethylbenzene)$Br_2]_2$, [Ru(hexamethylbenzene)$I_2]_2$, $RuCl_2(PPh_3)_3$, $RuBr_2(PPh_3)_3$, $RuI_2(PPh_3)_3$, $RuH_4(PPh_3)_3$, $RuClH(PPh_3)_3$, $RuH(OAc)(PPh_3)_3$, $RuH_2(PPh_3)_4$, and the like. In the above examples, DMSO represents dimethylsulfoxide, cod represents 1,5-cyclooctadiene, nbd represents norbornadiene, and Ph represents a phenyl group.

The ruthenium carbonyl complex represented by the general formula (21) can be easily prepared from a tridentate aminodiphosphine ligand and a ruthenium carbonyl complex as a precursor.

Examples of the ruthenium carbonyl complex as a precursor of the ruthenium carbonyl complex represented by the general formula (21) include the followings

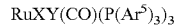
$RuXY(CO)(P(Ar^5)_3)_3$ (in the formula, $Ar^5$s each may be the same or different from one another and it represents an aryl group which may have a substituent group).

Examples of aryl group in $Ar^5$ include those aryl group that are explained above in relation to $R^1$, $R^2$, $R^3$, and $R^4$. Examples of the substituent group thereof also include those substituent groups that are explained above as suitable substituent groups of $R^1$, $R^2$, $R^3$, and $R^4$. Examples of the preferred $Ar^5$ include a phenyl group that may have a substituent group, the particularly a phenyl group. The ruthenium carbonyl complex as a precursor of the ruthenium carbonyl complex can be easily prepared by, for example, a method described in Inorg. Synth, 1974, 15, 45.

The tridentate aminodiphosphine ligand of the ruthenium carbonyl complex represented by the general formula (21) can be easily prepared by reacting a bis(substituted alkyl)amine having a leaving group with a phosphide compound of an alkali metal such as lithium, sodium, or potassium, for example.

Further, the ruthenium carbonyl complex in which an anionic ligand represented by X and an anionic ligand represented by Y in the ruthenium carbonyl complex represented by the general formula (21) are a hydride and Cl⁻, respectively, can be prepared by reacting $RuHCl(CO)(P(Ar^5)_3)_3$ and a tridentate aminodiphosphine ligand.

Further, the ruthenium carbonyl complex in which an anionic ligand represented by X and an anionic ligand represented by Y in the ruthenium carbonyl complex represented by the general formula (21) are a hydride and $BH_4^-$, respectively, can be prepared by reacting the ruthenium carbonyl complex represented by the general formula (21) in which X and Y are the same or different from each other and represent a hydride, an alkyloxy group, a cycloalkyloxy group, an aryloxy group, an aralkyloxy group, a hydroxy group, an acyloxy group, a sulfonyloxy group, or a halogen ion with a boron hydride compound, for example, $NaBH_4$ according to a method described in J. Am. Chem. Soc. 2005, 127, 516, for example.

A preferred example of the ruthenium complex of the present invention is the one represented by the following general formula (48):

RuHCl(CO)(L)     (48)

wherein (L) represents a tridentate aminodiphosphine represented by the above general formula (25). This complex is easily prepared by appropriately mixing the tridentate aminodiphosphine ligand L represented by the general formula (25) and $RuClH(CO)(PPh_3)_3$ in a solvent.

Another preferred example of the ruthenium carbonyl complex includes the complex represented by the following general formula (49)

$RuH(BH_4)(CO)(L)$     (49)

(in the formula, (L) represents a tridentate aminodiphoshine represented by above general formula (25)). The complex can be easily prepared by appropriately mixing the ruthenium carbonyl complex represented by the general formula (46) with a boron hydride compound, for example $NaBH_4$, in an appropriate solvent.

The complex prepared in such a manner as described above may have stereoisomers due to the coordination or conformation of the ligands. However, the complex used in the reaction according to the method of the invention can be any one of a mixture of these stereoisomers and a pure single isomer.

As a dehydrogenation oxidation catalyst, the ruthenium carbonyl complex can function with high efficiency under industrially advantageous and mild reaction conditions, for example at relatively low temperature.

The dehydrogenation oxidation reaction according to the method of the invention (it is also simply referred to as a "dehydrogenation reaction") can be any one of an intramolecular reaction occurring in single molecule, an intermolecular reaction involving plural molecules of the same type, or an intermolecular reaction involving different molecules of two or more types. Thus, the reacting compound of the dehydrogenation oxidation reaction of the invention may be a molecule of the same type or a mixture of molecules of two or more types.

According to the dehydrogenation oxidation reaction of the invention, a hydroxy group (OH) binds to a carbon atom to release hydrogen (i.e., two hydrogen atoms) from the compound having a hydrogen atom on the carbon, and as a result, a carbonyl group (C=O) like an aldehyde group or a keto group is generated. When a compound that is produced by a bonding between the carbonyl group generated by dehydrogenation or a carbonyl group originally present in substrate with a hydroxy group (OH) or an amino group (NH) that is present in the molecule or other molecule binds to a carbon atom to yield a hydroxy group (OH) having a hydrogen atom on the carbon atom, the dehydrogenation oxidation reaction further progresses. When such reaction occurs between molecules, a carbonyl compound having an ester group or an amide group is produced. When such reaction occurs within the same molecule, lactone or lactam is produced, Thus, the dehydrogenation oxidation reaction of the invention is applicable not only to an intramolecular reaction but also to an intermolecular reaction. Further, it can be applied for production of various compounds having a carbonyl group (C=O), i.e., esters, amides, lactones, and lactams as well as aldehydes and ketones.

Herein below, the dehydrogenation oxidation reaction of the invention is described in greater detail.

The method of the invention for producing aldehydes from primary alcohols by using the ruthenium carbonyl complex represented by the general formula (21) as a dehydrogenation oxidation catalyst is a method that is expressed with the following reaction scheme (A)

[Chem. 51]

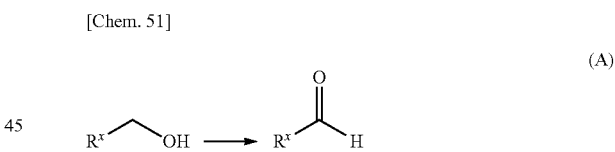

(A)

(in the formula, $R^X$ represents a hydrogen atom, an alkyl group, a cycloalkyl group, an aryl group, an aralkyl group, a heterocyclic group, an alkenyl group, an alkynyl group, a cycloalkenyl group, an oxycarbonyl group, a carboxamide group, a phosphono group, a phosphoryl group, a sulfonyl group, or a sulfo group, and the alkyl group, the cycloalkyl group, the aryl group, the aralkyl group, the heterocyclic group, the alkenyl group, the alkynyl group, the cycloalkenyl group, the oxycarbonyl group, the carboxamide group, the phosphono group, the phosphoryl group, the sulfonyl group, or the sulfo group may have a substituent group). This method of the invention is a method of producing aldehydes represented by the general formula (27) from the primary alcohols represented by the general formula (26) based on a dehydrogenation oxidation reaction.

$R^X$ in the chemical reaction scheme (A) is explained below.

Examples of the alkyl group, the cycloalkyl group, the aryl group, the aralkyl group, and the heterocyclic group as $R^X$ in the chemical reaction scheme (A) include the alkyl group, the cycloalkyl group, the aryl group, the aralkyl group, and the heterocyclic group that are explained above in relation to $R^1$, $R^2$, $R^3$, and $R^4$ of the general formula (22).

Examples of the alkenyl group include a linear or branched alkenyl group having 2 to 20 carbon atoms, preferably 2 to 15 carbon atoms, more preferably 2 to 10 carbon atoms. Specific examples thereof include an ethenyl group, a propenyl group, a 1-butenyl group, a pentenyl group, a hexenyl group, a heptenyl group, an octenyl group, a nonenyl group, and a decenyl group.

Examples of the alkynyl group include a linear or branched alkynyl group having 2 to 20 carbon atoms, preferably 2 to 15 carbon atoms, more preferably 2 to 10 carbon atoms. Specific examples thereof include an ethynyl group, a 1-propynyl group, a 2-propynyl group, a 1-butynyl group, a 3-butynyl group, a pentynyl group, and a hexynyl group.

Examples of the cycloalkenyl group include a 4- to 10-membered mono- to tricyclic aliphatic hydrocarbon group having one or two double bonds in the ring. Specific examples thereof include a cyclobutenyl group, a cyclopentenyl group, a cyclohexenyl group, a cycloheptenyl group, and a cyclooctenyl group.

Examples of the substituent groups that may be possessed by the alkyl group, the cycloalkyl group, the aryl group, the aralkyl group, and the heterocyclic group include the same groups as the substituent groups that may be possessed by $R^1$, $R^2$, $R^3$, and $R^4$ described above.

The oxycarbonyl group as $R^X$ in the chemical reaction scheme (A) include a group represented by the following the chemical formula (50),

[Chem. 52]

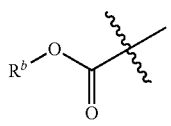

(50)

(in the formula, $R^b$ represents a hydrogen atom, an alkyl group, a cycloalkyl group, an aryl group, an aralkyl group, a heterocyclic group, an alkenyl group, an alkynyl group, a cycloalkenyl group, or a protective group for a carboxy group).

Examples of the alkyl group, the cycloalkyl group, the aryl group, the aralkyl group, and the heterocyclic group include the alkyl group, the cycloalkyl group, the aryl group, the aralkyl group, and the heterocyclic group that are explained above in relation to $R^1$, $R^2$, $R^3$, and $R^4$ of the general formula (22). Examples of the alkenyl group, the alkynyl group, and the cycloalkenyl group include the alkenyl group, the alkynyl group, and the cycloalkenyl group that are explained above in relation to $R^X$ of the reaction scheme (A) above. Further, examples of the protective group for a carboxy group include the groups that are described in Reference Literature 1 (Protective Groups in Organic Synthesis Second Edition, JOHN WILEY & SONS, INC. 1991), for example.

Examples of the oxycarbonyl group as $R^X$ in the chemical reaction scheme (A) include a methoxycarbonyl group, an ethoxycarbonyl group, a 2-propoxycarbonyl group, a cyclopentyloxycarbonyl group, a cyclohexyloxycarbonyl group, a phenoxycarbonyl group, a benzyloxycarbonyl group, a 4-pyridyloxycarbonyl group, a 3-pyrrolidyloxycarbonyl group, and a 3-pyrrolidyloxycarbonyl group.

Examples of the carboxamide group as $R^X$ in the chemical reaction scheme (A) include a group represented by the following chemical formula (51)

[Chem. 53]

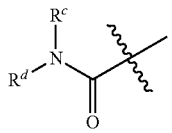

(51)

(in the formula, $R^c$ and $R^d$ may be the same or different from each other and represent a hydrogen atom, an alkyl group, a cycloalkyl group, an aryl group, an aralkyl group, a heterocyclic group, an alkenyl group, an alkynyl group, a cycloalkenyl group, an oxy group, a hydroxy group which may be protected, or a protective group for an amino group).

Examples of the alkyl group, the cycloalkyl group, the aryl group, the aralkyl group, and the heterocyclic group as $R^c$ and $R^d$ in the chemical formula (51) include the alkyl group, the cycloalkyl group, the aryl group, the aralkyl group, and the heterocyclic group that are explained above in relation to $R^1$, $R^2$, $R^3$, and $R^4$ of the general formula (22). Examples of the alkenyl group, the alkynyl group, and the cycloalkenyl group include the alkenyl group, the alkynyl group, and the cycloalkenyl group that are explained above in relation to $R^X$ of the reaction scheme (A) above.

Examples of the oxy group as $R^c$ and $R^d$ in the chemical formula (51) include a group represented by the chemical formula (52)

[Chem. 54]

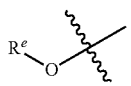

(52)

(in the formula, $R^e$ represents a hydrogen atom or the group that is explained above in relation to $R^b$ of the chemical formula (50) above).

Examples of the hydroxy group which may be protected as $R^c$ and $R^d$ of the chemical formula (51) include hydroxy groups that may be protected by protective groups for a hydroxy group, for example, protective groups for a hydroxy group described in Reference Literature 1 (Protective Groups in Organic Synthesis Second Edition, JOHN WILEY & SONS, INC. 1991).

Examples of the amino group which may be protected as $R^c$ and $R^d$ of the chemical formula (51) include amino groups that may be protected by protective groups for an amino group, for example, protective groups for an amino group described in Reference Literature 1 (Protective Groups in Organic Synthesis Second Edition, JOHN WILEY & SONS, INC. 1991).

Further, $R^c$ and $R^d$ of the chemical formula (51) may be linked to each other to form a ring.

Examples of the carboxamide group as $R^X$ in the chemical reaction scheme (A) include a carboxamide group, an N-methyl carboxamide group, an N,N-dimethyl carboxamide group, and a pyrrolidyl carboxamide group.

Examples of the phosphono group as $R^X$ in the chemical reaction scheme (A) include a group represented by the chemical formula (53)

[Chem. 55]

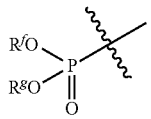

(53)

(in the formula, $R^f$ and $R^g$ may be the same or different from each other and represent a hydrogen atom, an alkyl group, a cycloalkyl group, an aryl group, an aralkyl group, a heterocyclic group, an alkenyl group, an alkynyl group, or a cycloalkenyl group).

Examples of the alkyl group, the cycloalkyl group, the aryl group, the aralkyl group, and the heterocyclic group in the chemical formula (53) include the alkyl group, the cycloalkyl group, the aryl group, the aralkyl group, the heterocyclic group, the alkenyl group, the alkynyl group, and the cycloalkenyl group that are explained above in relation to $R^1$, $R^2$, $R^3$, and $R^4$ of the general formula (22). There are examples of the alkyl group, the cycloalkyl group, the aryl group, the aralkyl group, and the heterocyclic group. Examples of the alkenyl group, the alkynyl group, and the cycloalkenyl group include the alkenyl group, the alkynyl group, and the cycloalkenyl group that are explained above in relation to $R^X$ of the reaction scheme (A) above.

Further, $R^f$ and $R^g$ of the chemical formula (53) may be linked to each other to form a ring.

Examples of the phosphono group as $R^X$ in the chemical reaction scheme (A) include a dimethylphosphono group, a diethylphosphono group, and a diphenylphosphono group.

Examples of the phosphoryl group as $R^X$ in the chemical reaction scheme (A) include a group represented by the chemical formula (54)

[Chem. 56]

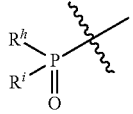

(54)

(in the formula, $R^h$ and $R^i$ may be the same or different from each other and examples thereof include the groups that are explained above in relation to $R^f$ and $R^g$ of the general formula (53)).

Further, $R^h$ and $R^i$ of the chemical formula (54) may be linked to each other to form a ring.

Examples of the phosphoryl group as $R^X$ in the chemical reaction scheme (A) include a dimethylphosphoryl group, a diethylphosphoryl group, and a diphenylphosphoryl group.

Examples of the sulfonyl group as $R^X$ in the chemical reaction scheme (A) include a group represented by the chemical formula (55)

[Chem. 57]

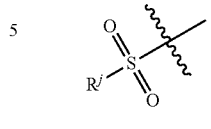

(55)

(in the formula, examples of $R^j$ include the groups that are explained above in relation to $R^f$ and $R^g$ of the general formula (53)).

Examples of the sulfonyl group as $R^X$ in the chemical reaction scheme (A) include a methane sulfonyl group, a benzene sulfonyl group, and a p-toluene sulfonyl group.

Examples of the sulfo group as $R^X$ in the chemical reaction scheme (A) include a group represented by the chemical formula (56)

[Chem. 58]

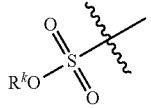

(56)

(in the formula, examples of $R^k$ include the groups that are explained above in relation to $R^f$ and $R^g$ of the general formula (53)).

Examples of the sulfo group as $R^X$ in the chemical reaction scheme (A) include a methyl sulfo group, an ethylsulfonyl group, and a phenylsulfonyl group.

The method of producing ketones from secondary alcohols by using, as a dehydrogenation oxidation catalyst, the ruthenium carbonyl complex represented by the general formula (21) of the invention is a method that is expressed with the following reaction scheme (B)

[Chem. 59]

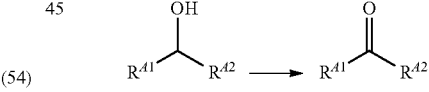

(B)

(in the formula, $R^{A1}$ and $R^{A2}$ may be the same or different from each other and represent a group that is explained above in relation to $R^X$ of the general formula (26) above, an oxy group, or a hydroxy group which may be protected. Further, $R^{A1}$ and $R^{A2}$ may be linked to each other to form a ring). This method of the invention is a method of producing ketones represented by the general formula (29) from the secondary alcohols represented by the general formula (28) based on a dehydrogenation oxidation reaction.

$R^{A1}$ and $R^{A2}$ in the chemical reaction scheme (B) are explained below.

Examples of the oxy group as $R^{A1}$ and $R^{A2}$ in the chemical reaction scheme (B) include the oxy group that is the same as the examples of the oxy group represented by the chemical formula (52) explained above in relation to the oxy group in $R^c$ and $R^d$ of the chemical formula (51).

Examples of the hydroxy group which may be protected in the chemical reaction scheme (B) include the hydroxy group which may be protected that is explained above as a hydroxy group which may be protected in relation to $R^c$ and $R^d$ of the chemical formula (51).

The method of producing esters from alcohols by using, as a dehydrogenation oxidation catalyst, the ruthenium carbonyl complex represented by the general formula (21) of the invention is a method that is expressed with the following reaction scheme (C)

[Chem. 60]

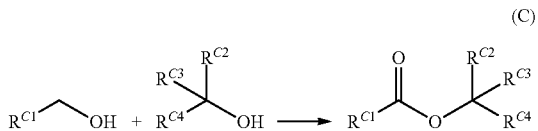

(C)

(in the formula, $R^{C1}$, $R^{C2}$, $R^{C3}$, and $R^{C4}$ may be the same or different from one another and represent a group that is explained above in relation to $R^X$ of the general formula (26) above. Further, $R^{C2}$ and $R^{C3}$ and/or $R^{C4}$ may be linked to each other to form a ring). This method of the invention is a method of producing esters represented by the general formula (32) from the primary alcohols represented by the general formula (30) and the tertiary alcohols represented by the general formula (31) based on a dehydrogenation oxidation reaction.

The method of producing esters from aldehydes by using, as a dehydrogenation oxidation catalyst, the ruthenium carbonyl complex represented by the general formula (21) of the invention is a method that is expressed with the following reaction scheme (D)

[Chem. 61]

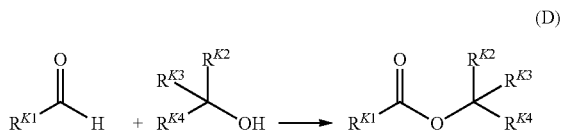

(D)

(in the formula, $R^{K1}$, $R^{K2}$, $R^{K3}$, and $R^{K4}$ may be the same or different from one another, $R^{K1}$ represents a hydrogen atom or a group that is explained above in relation to $R^{A1}$ and $R^{A2}$ of the general formula (28) above, and $R^{K2}$, $R^{K3}$, and $R^{K4}$ represent a group that is explained above in relation to $R^X$ of the general formula (26) above. Further, $R^{K2}$ and $R^{K3}$ and/or $R^{K4}$ may be linked to each other to form a ring). This method of the invention is a method of producing esters from the aldehydes represented by the general formula (33) and the alcohols represented by the general formula (34) based on a dehydrogenation oxidation reaction.

According to above method, the aldehydes that are used as a reacting compound may be produced in a reaction system by using primary alcohols, for example, the alcohols represented by the general formula (26). Thus, instead of using the aldehydes as a reacting compound of this method, it is also possible to react primary alcohols in a reaction system to give aldehydes.

The method of producing lactones from diols by using, as a dehydrogenation oxidation catalyst, the ruthenium carbonyl complex represented by the general formula (21) of the invention is a method that is expressed with the following reaction scheme (E)

[Chem. 62]

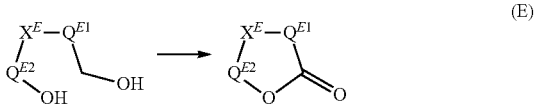

(E)

(in the formula, $Q^{E1}$ and $Q^{E2}$ may be the same or different from each other and represent a bonding arm, a divalent allylene group, or a divalent alkylene group, a divalent cycloalkylene group, or a divalent aralkylene group that are explained above in relation to $Q^1$ and $Q^2$ of the general formula (22) above, and the divalent allylene group may have a substituent group which is the same as the substituent groups that may be possessed by the divalent alkylene group, the divalent cycloalkylene group, or the divalent aralkylene group described above in relation to the general formula (22). $X^E$ is a bonding arm (with the proviso that $Q^{E1}$, $Q^{E2}$, $X^E$ do not simultaneously represent a bonding arm), an oxygen atom, a sulfur atom, —S(O)—, —S(O$_2$)—, or N—$R^E$ ($R^E$ represents the same group as $R^{K1}$ which is explained above in relation to the general formula (33), or a protective group that is described as a protective group for an amino in Reference Literature 1 (Protective Groups in Organic Synthesis Second Edition, JOHN WILEY & SONS, INC. 1991) described above). This method of the invention is a method of producing lactones represented by the general formula (37) from the diols represented by the general formula (36) through intramolecular cyclization based on a dehydrogenation oxidation reaction.

The method of producing amides from alcohols and amines by using, as a dehydrogenation oxidation catalyst, the ruthenium carbonyl complex represented by the general formula (21) of the invention is a method that is expressed with the following reaction scheme (F)

[Chem. 63]

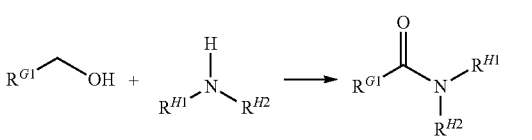

(F)

(in the formula, $R^{G1}$, $R^{H1}$ and $R^{H2}$ may be the same or different from one another, $R^{G1}$ represents a group that is explained above in relation to $R^X$ of the general formula (26) above, and $R^{H1}$ and $R^{H2}$ represent a group that is explained above in relation to $R^E$ in N—$R^E$ of the reaction scheme (E) above. Further, $R^{H1}$ and $R^{H2}$ may be linked to each other to form a ring). This method of the invention is a method of producing amides represented by the general formula (40) from the primary alcohols represented by the general formula (38) and the primary or secondary amines represented by the general formula (39) based on a dehydrogenation oxidation reaction.

The method of producing amides from aldehydes and amines by using, as a dehydrogenation oxidation catalyst, the ruthenium carbonyl complex represented by the general formula (21) of the invention is a method that is expressed with the following reaction scheme (G)

[Chem. 64]

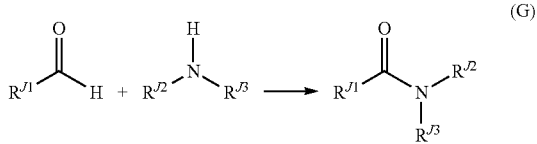

(G)

(in the formula, $R^{J1}$, $R^{J2}$, and $R^{J3}$ may be the same or different from one another, $R^{J1}$ represents a hydrogen atom or a group that is explained above in relation to $R^{A1}$ and $R^{A2}$ of the general formula (28) above, and $R^{J2}$ and $R^{J3}$ represent a group that is explained above in relation to $R^E$ in N—$R^E$ of the reaction scheme (E) above. Further, $R^{J1}$ and $R^{J2}$ may be linked to each other to form a ring). This method of the invention is a method of producing amides represented by the general formula (43) from the aldehydes represented by the general formula (41) and the primary or secondary amines represented by the general formula (42) based on a dehydrogenation oxidation reaction.

Also in the method above, the aldehydes that are used as a reacting compound may be produced in a reaction system by using primary alcohols, for example, the alcohols represented by the general formula (26). Thus, instead of using the aldehydes as a reacting compound of this method, it is also possible to react primary alcohols in a reaction system to give aldehydes.

The method of producing lactams from aminoalcohols by using, as a dehydrogenation oxidation catalyst, the ruthenium carbonyl complex represented by the general formula (21) of the invention is a method that is expressed with the following reaction scheme (H)

[Chem. 65]

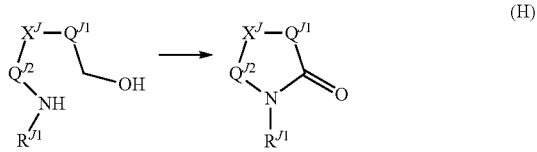

(H)

(in the formula, $Q^{J1}$ and $Q^{J2}$ may be the same or different from each other and represent a group which is the same as $Q^{E1}$ and $Q^{E2}$ that are explained above in relation to the reaction scheme (E), $X^J$ represents a group which is the same as $X^E$ that is explained above in relation to the reaction scheme (E) (with the proviso that $Q^{J1}$, $Q^{J2}$, and $X^J$ do not simultaneously represent a bonding arm), $R^{J1}$ represents a group which is the same as $R^{K1}$ that is explained above in relation to the general formula (33) or a protective group that is described as a protective group for an amino in Reference Literature 1 (Protective Groups in Organic Synthesis Second Edition, JOHN WILEY & SONS, INC. 1991) described above. This method of the invention is a method of producing lactams represented by the general formula (45) from the aminoalcohols represented by the general formula (44) through intramolecular cyclization based on a dehydrogenation oxidation reaction.

Provided by the invention is a method of producing a carbonyl compound like aldehydes, ketones, esters, lactones, amides, and lactams by using the ruthenium carbonyl complex described above as a dehydrogenation oxidation catalyst. Thus, when the compound having a carbonyl group as a reaction product of the method of the invention is represented by a general formula, it can be represented by the general formula (Z) above. Further, when $Y^K$ in the general formula (Z) is a bonding arm, aldehydes or ketones are produced. When $Y^K$ in the general formula (Z) is an oxygen atom, esters or lactones are produced. Further, when alcohols used as a reacting material to produce esters are $R^{P1}$—C($R^{T1}$)($R^{T2}$)—OH, $Y^K$ may be —O—C($R^{T1}$)($R^{T2}$)—. Further, when $Y^K$ is N—$R^Z$, amides or lactams are produced. It is preferable that $R^{P1}$, $R^{P2}$, $R^{T1}$, $R^{T2}$, and $R^Z$ in the general formula (Z) each independently represent a hydrogen atom, an alkyl group which may have a substituent group, a cycloalkyl group which may have a substituent group, an aryl group which may have a substituent group, an aralkyl group which may have a substituent group, a heterocyclic group which may have a substituent group, an alkenyl group which may have a substituent group, an alkynyl group which may have a substituent group, or a cycloalkenyl group which may have a substituent group, or $R^{P1}$ and $R^{P2}$ may be linked together to form a divalent alkylene group which may have a substituent group, a divalent cycloalkylene group which may have a substituent group, a divalent allylene group which may have a substituent group, or a divalent aralkylene group which may have a substituent group. Examples of the substituent group include those explained above.

The ruthenium carbonyl complex of the invention is a catalyst which is useful for producing a compound having a carbonyl group represented by the general formula (Z), in particular aldehydes, ketones, esters, lactones, amides, and lactams based on a dehydrogenation oxidation catalyst. Thus, also provided by the invention is a dehydrogenation oxidation catalyst consisting of the ruthenium carbonyl complex described above.

The alcohols, aldehydes, amines, diols, and aminoalcohols that are used as a reacting material for the production may be substituted with any substituent group as long as it has no adverse effect on the dehydrogenation oxidation of the invention. In addition, when the reacting material contains a substituent group which has an adverse effect on the reaction, it is possible to protect the corresponding substituent group with a protective group, if necessary.

As described above, although the method of the invention can be performed according to various modes, the basic mode for performing the method of the invention is to produce a carbonyl compound like aldehydes, ketones, esters, lactones, amides, and lactams by using the ruthenium carbonyl complex as a dehydrogenation oxidation catalyst. In addition, when a compound capable of having further intramolecular or intermolecular reaction is present, the carbonyl compound produced as described above undergoes the further intramolecular or intermolecular reaction to yield an ester or an amide.

According to the dehydrogenation oxidation reaction of the invention, a compound which serves as a hydrogen acceptor may be included in advance in a reaction system. Examples of the hydrogen accepting compound include a compound having a keto group like acetone, methyl isobutyl ketone (MIBK), cyclohexanone, 3-pentanone, and levulinic acid ester, but not limited thereto.

The method for dehydrogenation oxidation reaction according to the invention can be properly performed without any solvent or in a solvent, but is preferably performed in a solvent. The solvent to be used is preferably capable of dissolving the substrate and the catalyst, and may be a single solvent or a mixed solvent. Specific examples of such a solvent include: aromatic hydrocarbons such as toluene and xylene; ketones such as acetone, cyclohexanone, and 3-pentanone; aliphatic hydrocarbons such as hexane and heptane;

halogenated hydrocarbons such as methylene chloride and chlorobenzene; ethers such as diethyl ether, tetrahydrofuran, methyl tert-butyl ether, and cyclopentyl methyl ether, and; alcohols such as tert-butyl alcohol. Among them, aromatic hydrocarbons, ketones, ethers, and alcohols are preferable. Toluene, acetone, cyclohexanone, 3-pentanone, and tert-butyl alcohol are particularly preferable. The amount of the solvent to be used can be appropriately selected depending on, for example, reaction conditions. If necessary, the reaction is performed with stirring.

The amount of the catalyst to be used depends on, for example, the type of catalyst used, the type of alcohols used as a substrate, reaction conditions, or the like, but a molar ratio of a ruthenium metal to the alcohols as a substrate is usually 0.0001 mol % to 10 mol %, and preferably 0.002 mol % to 5 mol %. According to the method of the invention, the reaction temperature during oxidation (dehydrogenation) is 0 degree C. to 200 degrees C., preferably 30 degrees C. to 160 degrees C. If the reaction temperature is too low, there is a case where a large amount of the unreacted raw material remains. On the other hand, if the reaction temperature is too high, there is a case where decomposition of, for example, the raw material, the catalyst, and the like undesirably occurs.

According to the method of the invention, the reaction time for carrying out dehydrogenation oxidation is 30 minutes to 72 hours, preferably 2 hours to 24 hours, which makes it possible to achieve a sufficiently high raw material conversion ratio.

After the completion of the reaction, target carbonyl compounds can be obtained by using, singly or in combination, purification techniques usually used such as extraction, filtration, crystallization, distillation, and various chromatography techniques.

According to the present invention, the reaction may be performed by adding an appropriate additive.

An example of additive is a basic compound. Specific examples of the basic compound include amines such as triethylamine, diisopropylethylamine, N,N-dimethylaniline, piperidine, pyridine, 4-dimethylaminopyridine, 1,5-diazabicyclo[4.3.0]nona-5-ene, 1,8-diazabicyclo[5.4.0]undeca-7-ene, tri-n-butylamine, and N-methylmorpholine; alkali metal carbonates such as potassium carbonate, sodium carbonate, lithium carbonate, and cesium carbonate; alkaline-earth metal carbonates such as magnesium carbonate and calcium carbonate; alkali metal hydrogen carbonates such as sodium hydrogen carbonate and potassium hydrogen carbonate; alkali metal hydroxides such as sodium hydroxide, potassium hydroxide, and lithium hydroxide; alkaline-earth metal hydroxides such as magnesium hydroxide and calcium hydroxide; alkali metal alkoxides such as sodium methoxide, sodium ethoxide, sodium isopropoxide, sodium tert-butoxide, potassium methoxide, potassium ethoxide, potassium isopropoxide, potassium tert-butoxide, lithium methoxide, lithium isopropoxide, and lithium tert-butoxide; alkaline-earth metal alkoxides such as magnesium methoxide and magnesium ethoxide; and metal hydrides such as sodium hydride, potassium hydride and sodium borohydride.

Examples of the particularly preferred base include sodium methoxide, potassium tert-butoxide, sodium hydroxide, potassium hydroxide, lithium hydroxide, and sodium borohydride. In particular, when the anionic ligand represented by X or Y in the general formula (21) as a catalyst is a halogen ion or carboxylate, it is preferable to have one or more types of the basic compound described above.

EXAMPLES

The present invention will be described in detail with reference to the following Examples, but the present invention is not limited to these Examples.

It is to be noted that the reaction was evaluated by determining an isolated yield or a gas chromatography (GC) area percentage (%).

$^1$H-NMR spectrum and $^{31}$P-NMR spectrum were measured using MERCURY plus 300 manufactured by Varian.

Synthesis of Ruthenium Carbonyl Complex Having Tridentate Ligand

Example 1

The ruthenium carbonyl complex 2 and 1 were produced according to the following reaction scheme.

[Chem. 66]

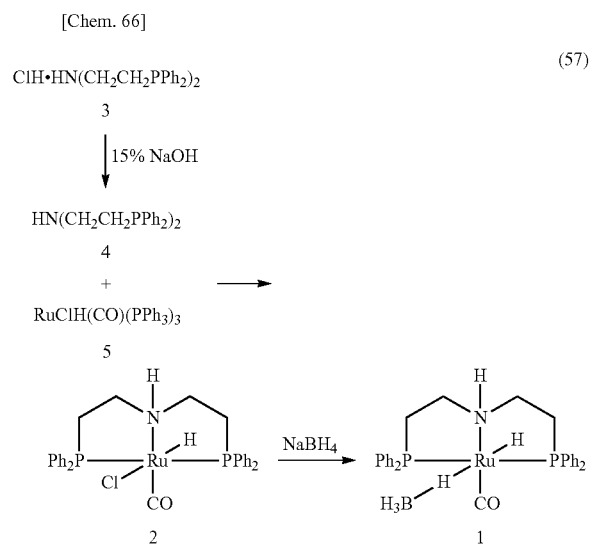

(57)

Under the stream of nitrogen, 4.18 mmol of amine hydrochloride 3 was placed in a 100 mL flask and suspended in 33 mL of toluene, and 14 mL of 15% aqueous NaOH solution was added thereto and the resulting mixture was stirred at room temperature until no solid remained. The resulting solution was separated into an organic phase and an aqueous phase, and the organic phase was washed with 14 mL of distilled water (2 times) and the aqueous phase was subjected to extraction with 14 mL of toluene (2 times). The thus obtained organic phases were combined and dried over sodium sulfate, and then the solvent was distilled off to obtain amine 4.

4.18 mmol of the ruthenium carbonyl complex 5 was placed in a 200 mL flask, and the flask was purged with nitrogen. Then, the amine 4 dissolved in 33 mL of toluene was added to the flask, and the resulting mixture was heated under reflux for 60 minutes. 82 mL of hexane was added, and then a crystal was separated by filtration under an atmosphere of nitrogen. The thus obtained crystal was washed with 10 mL of hexane and 40 mL of ethanol, and dried under a reduced pressure to obtain 1.4 g (2.3 mmol) of the ruthenium carbonyl complex 2.

$^1$H-NMR (300 MHz CD$_2$Cl$_2$): δ=−15.23 (t, J=29.3 Hz, 1H), 2.40-2.65 (m, 4H), 2.90-3.05 (m, 2H), 3.30-3.55 (m,

2H), 3.92 (bs, 1H), 7.08-7.34 (m, 4H), 7.38-7.46 (m, 8H), 7.40-7.88 (m, 8H)

$^{31}$P-NMR (121.5 MHz CD$_2$Cl$_2$): δ=52.8 (d, J=14 Hz)

2.22 mmol of the complex 2 which has been produced from the above was placed in a 1000 mL flask under nitrogen stream and suspended in 222 mL of toluene. Thereafter, NaBH$_4$ (60.0 mmol) dissolved in 222 mL of ethanol was added to the suspension and stirred for 30 minutes at 65 degrees C. The mixture was stirred for 30 minutes at room temperature and the solvent was distilled off under reduced pressure. 220 mL of hexane and 110 mL of distilled water were added, stirred for 15 min, and filtered. The resulting crystal was washed with 110 mL of water (2 times) and 110 mL of hexane (2 times). The resultant was dried under a reduced pressure to obtain 1.05 g (1.79 mmol) of the desired ruthenium carbonyl complex 1.

$^1$H-NMR (300 MHz CD$_2$Cl$_2$): δ=−12.36 (t, J=28.5 Hz, 1H), −2.80-1.70 (bs, 4H), 2.40-2.78 (m, 4H), 2.90-3.05 (m, 2H), 3.32-3.60 (m, 2H), 4.20-4.40 (m, 1H), 6.92-7.28 (m, 4H), 7.38-7.46 (m, 8H), 7.70-7.82 (m, 8H)

$^{31}$P-NMR (121.5 MHz CD$_2$Cl$_2$): δ=56.6 (s)

Production of Aldehydes

Example 2

Production of 1-octanal

[Chem. 67]

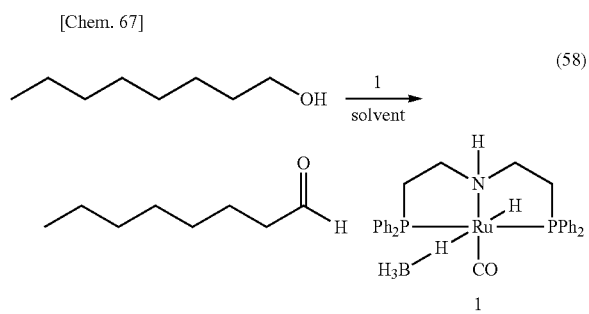

(58)

5.9 mg (1 mol %) of the ruthenium complex 1 which has been produced in the Example 1 were added to a 200 mL flask with a branched neck in which boiling chips are added. The flask with a branched neck is purged with nitrogen and 157 μL (1.0 mmol, 130 mg) of 1-octanol was added to the flask. Subsequently, 100 mL (0.01M) of acetone was added thereto. Under nitrogen stream, the mixture was then reacted under stirring with heating in an oil bath which is set at 60 degrees C. As a result of analysis of the reaction solution, it was found that 82% of octanal was produced.

Examples 3 and 4

Production of 1-octanal

1-Octanal was produced with reference to the method described in the Example 1 except that the amount of the catalyst, reaction time, and solvent are changed. The results are given in the following Table 1.

TABLE 1

| Example No. | Substrate (mmol) | 1 (mol %) | Solvent (ml) | Time (hr) | Yield (%) |
|---|---|---|---|---|---|
| 3 | 2.5 | 0.2 | Cyclohexanone (250) | 4 | 69 |
| 4 | 2.5 | 0.2 | Cyclohexanone (250) | 21 | 77 |

Apparatus and conditions that are employed for the analysis of the Examples 2 to 4 are as follows.

GC instrument: Shimadzu GC-2010
GC: Capillary of Neutra Bond-1
Injection temperature: 200 degrees C., Detection temperature: 280 degrees C.
Oven: 40 degrees C. (0 minutes)-100 degrees C. (5 degrees C./min)-280 degrees C. (10 degrees C./min)-280 degrees C. (10 minutes)

Examples 5 to 9

Production of Benzaldehyde

Benzaldehyde was produced according to the following reaction scheme.

[Chem. 68]

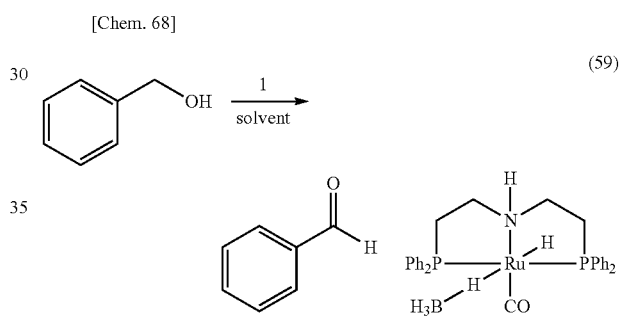

(59)

The ruthenium complex 1 which has been produced in the Example 1 was added to a glass vessel in which boiling chips are added. Subsequently, benzyl alcohol and the solvent described the Table 2 below were added thereto. The mixture was then stirred with heating under the reaction condition described in the Table 2. The results are given in the following Table 2.

TABLE 2

| Example No. | Substrate (mmol) | 1 (mol %) | Solvent (ml) | Temparature (° C.) | Time (hr) | Yield (%) |
|---|---|---|---|---|---|---|
| 5 | 1.0 | 1.0 | Acetone (20) | 60 | 3 | 78 |
| 6 | 1.0 | 1.0 | Cyclohexanone (2) | 120 | 3 | 69 |
| 7 | 1.0 | 1.0 | Cyclohexanone (2) | 157 | 1 | 76 |
| 8 | 5.0 | 0.2 | Cyclohexanone (10) | 157 | 1 | 76 |
| 9 | 5.0 | 0.2 | Cyclohexanone (10) | 157 | 3 | 73 |

For the analysis of the Examples 5 to 9, the apparatus and the conditions that are the same as those used for the analysis of the Examples 2 to 4 were employed.

Examples 10 and 11

Production of Cinnamaldehyde

Cinnamaldehyde was produced according to the following reaction scheme with reference to the method described in the Example 5.

[Chem. 69]

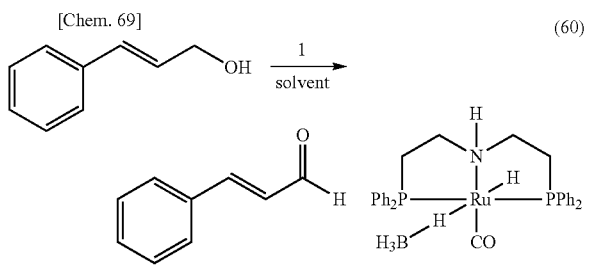

(60)

The results are given in the following Table 3.

TABLE 3

| Example No. | Substrate (mmol) | 1 (mol %) | Solvent (ml) | Temparature (° C.) | Time (hr) | Yield (%) |
|---|---|---|---|---|---|---|
| 10 | 1.0 | 1 | Cyclohexanone (2) | 120 | 3 | 77 |
| 11 | 1.0 | 1 | Cyclohexanone (2) | 157 | 1 | 84 |

Apparatus that is employed for the analysis of the Examples 10 and 11 is as follows.

GC instrument: Shimadzu GC-2010
GC: Capillary of Neutra Bond-1
Injection temperature: 200 degrees C., Detection temperature: 280 degrees C.
Oven: 40 degrees C. (0 minutes)-100 degrees C. (5 degrees C./min)-280 degrees C. (10 degrees C./min)-280 degrees C. (10 minutes)

As described above, according to the method of the invention, target aldehydes can be produced from various primary alcohols with excellent conversion ratio and excellent selectivity.

Production of Ketones

Example 12

Production of Acetophenone

Ketones were produced according to the following reaction scheme.

[Chem. 70]

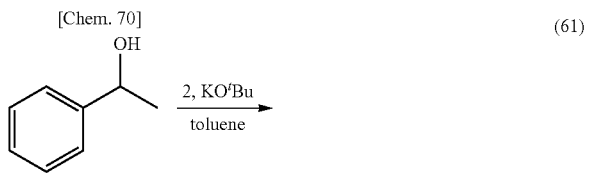

(61)

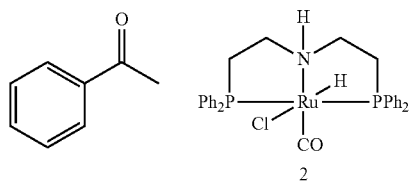

6.1 mg (0.01 mol) of the ruthenium complex 2 which has been produced in the Example 1 were added to a 50 mL flask with a branched neck in which boiling chips are added. 22.4 mg of KO$^t$Bu was added to the flask, and 1.21 mL (10 mmol, 1.22 g) of 1-phenylethanol was further added thereto. Subsequently, 20 mL of toluene was added thereto and the mixture was then reacted for 5 hours under stirring with heating in an oil bath which is set at 120 degrees C. As a result of analysis of the reaction solution, it was found that 69% of acetophenone was produced.

Example 13

Acetophenone was produced according to the following reaction scheme by using the ruthenium complex 1.

[Chem. 71]

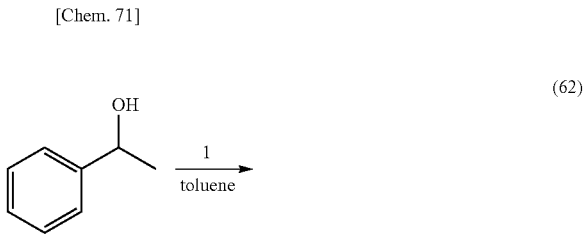

(62)

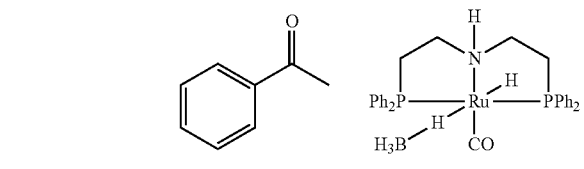

5.9 mg (0.01 mmol) of the ruthenium complex 1 which has been produced in the Example 1 were added to a 50 mL flask with a branched neck in which boiling chips are added. 1.21 mL (10 mmol, 1.22 g) of 1-phenylethanol was further added thereto. Subsequently, 20 mL of toluene was added thereto and the mixture was then reacted for 3 hours under stirring with heating in an oil bath which is set at 120 degrees C. As a result of analysis of the reaction solution, it was found that 35% of acetophenone was produced.

Apparatus that is employed for the analysis of the Examples 12 and 13 is as follows.

GC instrument: Shimadzu GC-2010
GC: capillary CP-Chirasil-Dex CB
Injection temperature: 250 degrees C., Detection temperature: 250 degrees C.
Oven: 120 degrees C. (15 minutes)

Examples 14 to 21

Production of Various Ketones by Using the Complex 2 as a Catalyst

Various ketones were produced according to the following reaction scheme by using the complex 2 as a catalyst.

[Chem. 72]

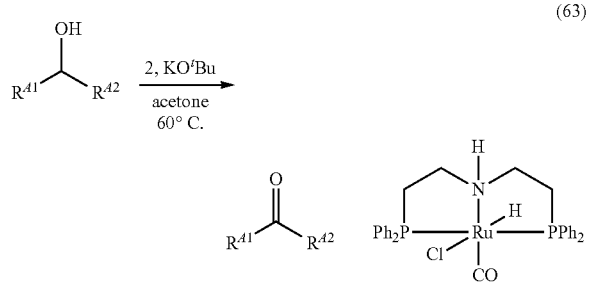

(63)

The ruthenium complex 2 which has been produced in the Example 1 and KO$^t$Bu were added to a Schlenk flask in which boiling chips are added. Subsequently, the substrate described the Table 4 below and acetone were added thereto. The mixture was then stirred at 60 degrees C. under nitrogen stream. As a result, the ketones that correspond to the reacting compound (i.e., substrate) described in the Table 4 were obtained. The results are given in the following Table 4.

TABLE 4

| Example No. | Substrate (mmol) | 2 (mol %) | Acetone (ml) | KO$^t$Bu (mol %) | Time (hr) | Yield (%) |
|---|---|---|---|---|---|---|
| 14 | Ph-CH$_2$CH$_2$-CH(OH)-CH$_3$  1.0 | 1 | 2 | 10 | 1 | 95 |
| 15 | H$_3$C(CH$_2$)$_7$-CH(OH)-CH(CH$_3$)$_2$  1.0 | 1 | 2 | 10 | 1 | 97 |
| 16 | H$_3$C(CH$_2$)$_5$-CH(OH)-CH(CH$_3$)$_2$  10.0 | 0.1 | 20 | 1 | 5 | 97 |
| 17 | Ph$_2$CHOH  1.0 | 1 | 2 | 10 | 1 | 93 |
| 18 | cyclohexanol  10.0 | 0.1 | 20 | 10 | 16 | 60 |
| 19 | cycloheptanol  1.0 | 1 | 2 | 10 | 1 | 97 |
| 20 | 3-quinuclidinol  1.0 | 1 | 2 | 10 | 1 | 95 |
| 21 | isopulegol-type cyclohexenol  1.0 | 1 | 2 | 10 | 1 | 89 |

Apparatus that is employed for the analysis of the Examples 14 and 15 is as follows.
GC instrument: Shimadzu GC-2010
GC: capillary CP-Chirasil-Dex CB
Injection temperature: 250 degrees C., Detection temperature: 250 degrees C.
Oven: 120 degrees C. (30 min)

Apparatus that is employed for the analysis of the Examples 16 and 18 is as follows.
GC instrument: Hewlett Packard 5890 series II
GC: capillary TC-WAX
Injection temperature: 250 degrees C., Detection temperature: 250 degrees C.
Oven: 60 degrees C. (0 min)-140 degrees C. (5 degrees C./min)-140 degrees C. (4 min)

Apparatus that is employed for the analysis of the Example 17 is as follows.
GC instrument: Shimadzu GC-2010 plus
GC: capillary CP-Chirasil-Dex CB
Injection temperature: 250 degrees C., Detection temperature: 250 degrees C.
Oven: 160 degrees C. (30 min)

Apparatus that is employed for the analysis of the Example 19 is as follows.
GC instrument: Shimadzu GC-2010 plus
GC: capillary CP-Chirasil-Dex CB
Injection temperature: 250 degrees C., Detection temperature: 250 degrees C.
Oven: 110 degrees C. (30 min)

Apparatus that is employed for the analysis of the Example 20 is as follows.
GC instrument: Shimadzu GC-2010
GC: Capillary of Neutra Bond-1
Injection temperature: 200 degrees C., Detection temperature: 280 degrees C.

Oven: 130 degrees C. (0 min)-250 degrees C. (5 degrees C./min)-250 degrees C. (11 min)

Apparatus that is employed for the analysis of the Example 21 is as follows.

GC instrument: Shimadzu GC-2010 plus

GC: capillary CP-Chirasil-Dex CB

Injection temperature: 250 degrees C., Detection temperature: 250 degrees C.

Oven: 130 degrees C. (30 min)

Examples 22 to 29

Production of Various Ketones Using the Complex 1

Various ketones were produced according to the following reaction scheme by using the complex 1 as a catalyst.

[Chem. 73]

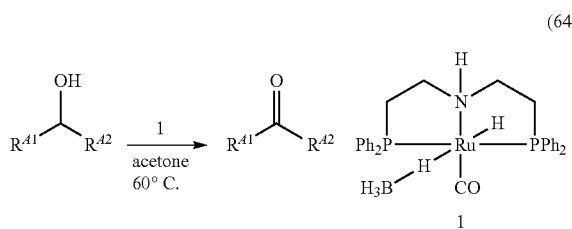

(64)

The ruthenium complex 1 which has been produced in the Example 1 was added to a Schlenk flask in which boiling chips are added. Subsequently, the substrate described the Table 5 below and acetone were added thereto. The mixture was then stirred at 60 degrees C. under nitrogen stream. As a result, the ketones that correspond to the reacting compound (i.e., substrate) described in the Table 5 were obtained. The results are given in the following Table 5.

TABLE 5

| Example No. | Substrate (mmol) | 2 (mol %) | Acetone (ml) | Time (hr) | Yield (%) |
|---|---|---|---|---|---|
| 22 | 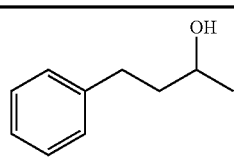 1.0 | 1 | 2 | 1 | 95 |
| 23 | H$_3$C(CH$_2$)$_7$ OH 1.0 | 1 | 2 | 1 | 95 |
| 24 | H$_3$C(CH$_2$)$_5$ OH 10.0 | 0.1 | 20 | 5 | 81 |

TABLE 5-continued

| Example No. | Substrate (mmol) | 2 (mol %) | Acetone (ml) | Time (hr) | Yield (%) |
|---|---|---|---|---|---|
| 25 | Ph$_2$CHOH 1.0 | 1 | 2 | 3 | 81 |
| 26 | cyclohexanol 10.0 | 0.1 | 20 | 16 | 72 |
| 27 | cycloheptanol 1.0 | 1 | 2 | 1 | 99 |
| 28 | 3-quinuclidinol 1.0 | 1 | 2 | 1 | 83 |
| 29 | 1-phenylethanol 50.0 | 0.01 | 0.2 | 21 | 83 |

Conditions for the Examples 22, 23, and 29 are the same as those described for the Example 14. Conditions for the Example 24 are the same as those described for the Example 16. Conditions for the Example 25 are the same as those described for the Example 17. Conditions for the Example 26 are the same as those described for the Example 16. Conditions for the Example 27 are the same as those described for the Example 19. Conditions for the Example 28 are the same as those described for the Example 20.

Production of Esters

Example 30

Production of Butyl Butanoate by Using Complex 2

Esters were produced according to the following reaction scheme.

[Chem. 74]

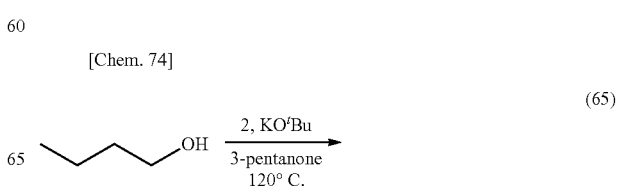

(65)

-continued

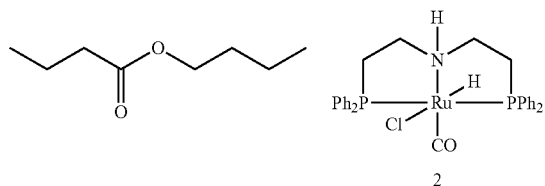

2

6.1 mg (0.01 mmol) of the ruthenium complex 2 which has been produced in the Example 1 and KO$^t$Bu (11.2 mg, 0.1 mmol) were added to a 15 mL test tube in which boiling chips are added. 5.0 mL of 3-pentanone was further added thereto. Subsequently, 1-butanol (915 μL, 10 mmol) was measured and added thereto and the mixture was then reacted for 9 hours under stirring with heating in an oil bath which is set at 120 degrees C. As a result of analysis of the reaction solution, it was found that 62% of butyl butanoate was produced.

Example 31

Production of Butyl Butanoate by Using Complex 1

Esters were produced according to the following reaction scheme.

[Chem. 75]

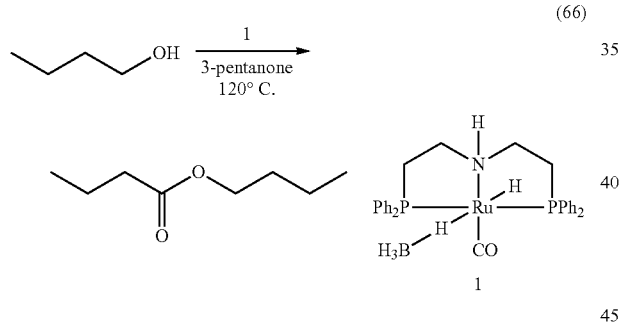

(66)

5.9 mg (0.01 mmol) of the ruthenium complex 1 which has been produced in the Example 1 was added to a 15 mL test tube in which boiling chips are added. 5.0 mL of 3-pentanone was further added thereto. Subsequently, 1-butanol (915 μL, 10 mmol) was added thereto and the mixture was then reacted for 9 hours under stirring with heating in an oil bath which is set at 120 degrees C. As a result of analysis of the reaction solution, it was found that 100% of butyl butanoate was produced.

Apparatus that is employed for the analysis of the Examples 30 and 31 is as follows.

GC instrument: Hewlett Packard 5890 Series II

GC: capillary TC-WAX

Injection temperature: 250 degrees C., Detection temperature: 250 degrees C.

Oven: 40 degrees C. (0 min)-80 degrees C. (5 degrees C./min)-250 degrees C. (10 degrees C./min)-250 degrees C. (5 min)

Example 32

Production of Methyl Benzoate by Using Complex 1

Methyl benzoate was produced according to the following reaction scheme.

[Chem. 76]

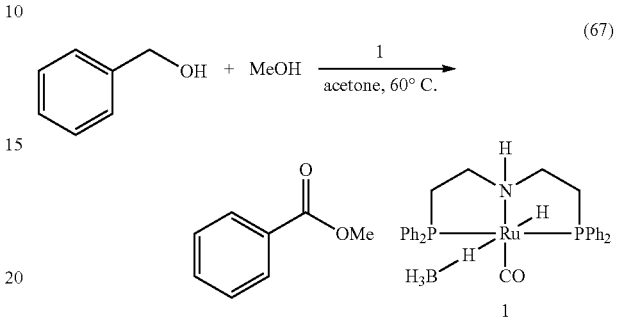

(67)

5.9 mg (0.01 mmol) of the ruthenium complex 1 which has been produced in the Example 1 was added to a 15 mL test tube in which boiling chips are added. 2.9 mL of acetone and 40.6 μL (10 mmol) of methanol were further added thereto. Subsequently, benzyl alcohol (103 μL, 1 mmol) was added thereto and the mixture was then reacted for 16 hours under stirring with heating in an oil bath which is set at 60 degrees C. As a result of analysis of the reaction solution, it was found that 38% of methyl benzoate was produced.

For the analysis of the Example 32, the apparatus and the conditions that are the same as those used for the analysis of the Examples 2 to 4 were employed.

Production of Lactones

Examples 33 to 36

Production of Lactones by Using the Complex 2

Various lactones were produced according to the following reaction scheme.

[Chem. 77]

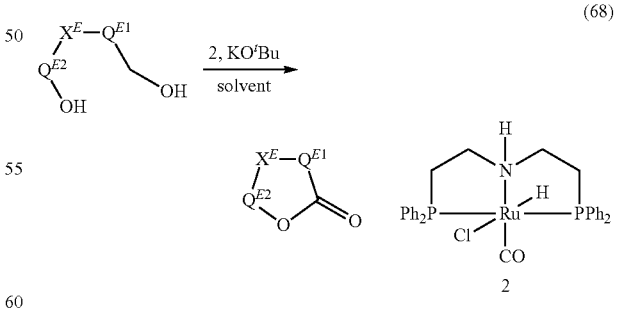

(68)

The ruthenium complex 2 which has been produced in the Example 1 and KO$^t$Bu were added to a Schlenk flask in which boiling chips are added. Subsequently, the substrate described the Table 6 below and solvent were added thereto. The mixture was then stirred under nitrogen stream. The results are given in the following Table 6.

TABLE 6

| Example No. | Substrate (mmol) | 2 (mol %) | Solvent (ml) | KO^tBu (mol %) | Time (hr) | Temperature (° C.) | Yield (%) |
|---|---|---|---|---|---|---|---|
| 33 | HO-(CH2)4-OH  1.0 | 1 | Toluene 2 | 10 | 1 | 12 | 98 |
| 34 | HO-(CH2)4-OH  100 | 0.005 | Toluene 200 | 0.1 | 3 | reflux | 100 |
| 35 | benzene-1,2-bis(CH2OH)  1.0 | 1 | Acetone 2 | 10 | 1 | 60 | 90 |
| 36 | benzene-1,2-bis(CH2OH)  1.0 | 1 | Toluene 2 | 10 | 1 | 120 | 100 |

Examples 37 to 43

Production of Lactones by Using the Complex 1

Various lactones were produced according to the following reaction scheme.

[Chem. 78]

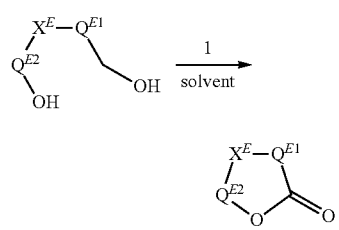

(69)

The ruthenium complex 1 which has been produced in the Example 1 was added to a Schlenk flask in which boiling chips are added. Subsequently, the substrate described the Table 7 below and solvent were added thereto. The mixture was then stirred under nitrogen stream. The results are given in the following Table 7.

TABLE 7

| Example No. | Substrate (mmol) | 1 (mol %) | Solvent (ml) | Time (hr) | Temperature (° C.) | Yield (%) |
|---|---|---|---|---|---|---|
| 37 | HO-(CH2)4-OH  1.0 | 1 | Acetone 2.0 | 1 | 60 | 91 |
| 38 | HO-(CH2)4-OH  1.0 | 1 | Toluene 2.0 | 1 | 120 | 98 |

TABLE 7-continued

| Example No. | Substrate (mmol) | 1 (mol %) | Solvent (ml) | Time (hr) | Temparature (° C.) | Yield (%) |
|---|---|---|---|---|---|---|
| 39 | HO-(CH2)4-OH  5.0 | 0.1 | Toluene 20 | 3 | 120 | 100 |
| 40 | HO-(CH2)4-OH  50 | 0.01 | Toluene 100 | 5 | 120 | 100 |
| 41 | HO-(CH2)4-OH  100 | 0.005 | Toluene 200 | 3 | reflux | 100 |
| 42 | 1,2-bis(hydroxymethyl)benzene  1.0 | 1 | Toluene 2.0 | 1 | 120 | 100 |
| 43 | 1,2-bis(hydroxymethyl)benzene  10.0 | 0.1 | Toluene 20 | 3 | 120 | 100 |

For the analysis of the Examples 33 to 34 and 37 to 41, the apparatus and the conditions that are the same as those used for the analysis of the Examples 2 to 4 were employed.

Apparatus that is employed for the analysis of the Examples 35, 36, 42 and 43 is as follows.

GC instrument: Shimadzu GC-2010

GC: Capillary of Neutra Bond-1

Injection temperature: 200 degrees C., Detection temperature: 280 degrees C.

Oven: 120 degrees C. (30 min)

Production of Lactams

Example 44

Production of δ-valerolactam by Using the Complex 1

δ-Valerolactam was produced according to the following reaction scheme.

[Chem. 79]

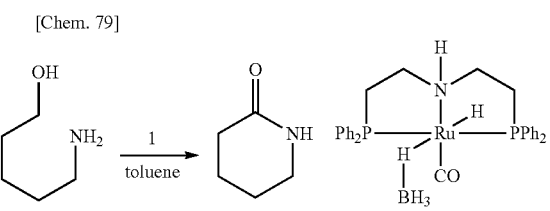

5.9 mg (0.01 mmol) of the ruthenium complex 1 which has been produced in the Example 1 was added to a 30 mL Schlenk flask in which boiling chips are added. Subsequently, 10 mL of toluene was added thereto and the mixture was then reacted for 3 hours under stirring with heating in an oil bath which is set at 120 degrees C. As a result of analysis of the reaction solution, it was found that 100% of δ-valerolactam was produced.

For the analysis of the Example 44, the apparatus and the conditions that are the same as those used for the analysis of the Examples 2 to 4 were employed.

INDUSTRIAL APPLICABILITY

The invention is to provide a novel catalyst for dehydrogenation which can be easily produced and has high catalytic efficiency, and a method of producing a compound having a carbonyl group using the catalyst. As they are useful for various fields of industrial organic chemistry, they have an industrial applicability.

The invention claimed is:

1. A method for producing a compound having a carbonyl group by dehydrogenation oxidation of a reacting compound in the presence of a dehydrogenation oxidation catalyst which comprises the ruthenium carbonyl complex represented by the following general formula (21)

$$RuXY(CO)(L) \tag{21}$$

(in the formula, X and Y may be the same or different from each other and each represents an anionic ligand and L represents a tridentate aminodiphosphine ligand represented by the following general formula (22)

[Chem. 1]

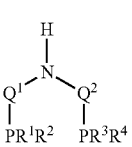

(22)

(in the formula, $R^1$, $R^2$, $R^3$, and $R^4$ may be the same or different from one another and each represents a hydrogen atom, an alkyl group, a cycloalkyl group, an aryl group, an aralkyl group, an alkyloxy group, a cycloalkyloxy group, an aryloxy group, an aralkyloxy group, a heterocyclic group, or a substituted amino group, the $R^1$ and $R^2$ and/or $R^3$ and $R^4$ may be linked together to form a ring with an adjacent phosphorus atom, the alkyl group, the cycloalkyl group, the aryl group, the aralkyl group, the alkyloxy group, the cycloalkyloxy group, the aryloxy group, the aralkyloxy group, the heterocyclic group, and the substituted amino group may have a substituent group, $Q^1$ and $Q^2$ may be the same or different from each other and each represents a divalent alkylene group that may have a substituent group, a divalent cycloalkylene group that may have a substituent group, or a divalent aralkylene group that may have a substituent group)).

2. The production method according to claim 1, wherein the tridentate aminodiphosphine ligand L of the ruthenium carbonyl complex is a tridentate aminodiphosphine ligand L represented by the following general formula (24)

[Chem. 2]

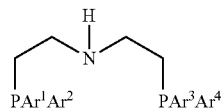

(24)

(in the formula, $Ar^1$, $Ar^2$, $Ar^3$, and $Ar^4$ may be the same or different from one another and each represents an aryl group or an aromatic heterocyclic group, and the aryl group and the aromatic heterocyclic group may have a substituent group).

3. The production method according to claim 2, wherein $Ar^1$, $Ar^2$, $Ar^3$, and $Ar^4$ in the general formula (24) are each a phenyl group that may have a substituent group.

4. The production method according to claim 1, wherein the tridentate aminodiphosphine ligand L of the ruthenium carbonyl complex is an optically active tridentate aminodiphosphine ligand.

5. The production method according to claim 1, wherein the anionic ligand represented by X in the general formula (21) is a hydride and the anionic ligand represented by Y in the general formula (21) is Cl.

6. The production method according to claim 1, wherein the anionic ligand represented by X in the general formula (21) is a hydride and the anionic ligand represented by Y in the general formula (21) is $BH_4$.

7. The production method according to claim 1, wherein the dehydrogenation oxidation reaction is carried out in the presence of a base.

* * * * *